(12) United States Patent
Chen et al.

(10) Patent No.: US 12,144,715 B2
(45) Date of Patent: Nov. 19, 2024

(54) SOFT TISSUE GRAFTS, AND METHODS OF MAKING AND USING SAME

(71) Applicant: LifeNet Health, Virginia Beach, VA (US)

(72) Inventors: Jingsong Chen, Virginia Beach, VA (US); Joshua Jones, Virginia Beach, VA (US); Kent Bockes, Black Mountain, NC (US); John Garrettson, Chesapeake, VA (US); Arthur L. Brame, Virginia Beach, VA (US); Thomas Sander, Hamas, UT (US); Beau Inskeep, Virginia Beach, VA (US); Amy Dorfman, Virginia Beach, VA (US)

(73) Assignee: LifeNet Health, Virginia Beach, VA (US)

( * ) Notice: Subject to any disclaimer, the term of this patent is extended or adjusted under 35 U.S.C. 154(b) by 607 days.

(21) Appl. No.: 17/308,259

(22) Filed: May 5, 2021

(65) Prior Publication Data
US 2021/0267743 A1   Sep. 2, 2021

Related U.S. Application Data

(63) Continuation of application No. 15/534,237, filed as application No. PCT/US2016/057038 on Oct. 14, 2016, now Pat. No. 11,058,530.
(Continued)

(51) Int. Cl.
*A61F 2/08* (2006.01)
*A61F 2/00* (2006.01)
(Continued)

(52) U.S. Cl.
CPC .............. *A61F 2/0077* (2013.01); *A61F 2/08* (2013.01); *A61F 2/12* (2013.01); *A61L 27/3604* (2013.01);
(Continued)

(58) Field of Classification Search
CPC ........ A61F 2/0063; A61F 2/12; A61F 2/0077; A61F 2/08; A61F 2002/0068;
(Continued)

(56) References Cited

U.S. PATENT DOCUMENTS 4,840,629 A   6/1989 Bustos
5,356,429 A   10/1994 Seare
(Continued)

FOREIGN PATENT DOCUMENTS

WO   2009146072 A1   12/2009
WO   2015065923 A1   5/2015

OTHER PUBLICATIONS

Extended European Search Report for European Application No. 23 174 616.5, dated Jul. 11, 2023, 6 pages.
(Continued)

*Primary Examiner* — Katherine H Schwiker
(74) *Attorney, Agent, or Firm* — Matney Legal Group PLLC

(57) ABSTRACT

Soft tissue grafts, packaged soft tissue grafts, and methods of making and using soft tissue grafts are disclosed. One soft tissue graft includes processed tissue material having first and second opposed surfaces. The first and second opposed surfaces are bounded by first and second edges. The first edge has a concave shape that curves toward the second edge. The second edge has a convex shape that curves away from the first edge. The first surface comprises a plurality of apertures. At least one of the apertures is formed from a multi-directional separation in the first surface. One method
(Continued)

of making a soft tissue graft includes positioning a cutting die on a surface of tissue material, pressing the cutting die into the tissue material to cut the tissue material, and processing the cut tissue material to create processed tissue material.

17 Claims, 15 Drawing Sheets

Related U.S. Application Data

(60) Provisional application No. 62/257,582, filed on Nov. 19, 2015, provisional application No. 62/242,930, filed on Oct. 16, 2015.

(51) Int. Cl.
 *A61F 2/12* (2006.01)
 *A61L 27/36* (2006.01)
 *A61L 27/50* (2006.01)

(52) U.S. Cl.
 CPC ......... *A61L 27/3691* (2013.01); *A61L 27/502* (2013.01); *A61F 2002/0081* (2013.01); *A61F 2002/0086* (2013.01); *A61F 2/0095* (2013.01); *A61F 2210/0004* (2013.01); *A61F 2210/0057* (2013.01); *A61F 2210/0076* (2013.01); *A61F 2230/0013* (2013.01); *A61F 2230/0028* (2013.01); *A61F 2230/0034* (2013.01); *A61F 2230/0041* (2013.01); *A61F 2230/0043* (2013.01); *A61F 2240/00* (2013.01); *A61F 2240/002* (2013.01); *A61L 2430/34* (2013.01); *A61L 2430/40* (2013.01)

(58) Field of Classification Search
 CPC ...... A61F 2002/0081; A61F 2210/0076; A61F 2210/0057; A61F 2230/0013; A61F 2230/0034; A61L 27/502
 See application file for complete search history.

(56) References Cited

U.S. PATENT DOCUMENTS

| | | | |
|---|---|---|---|
| 5,954,767 A | 9/1999 | Pajotin et al. | |
| 6,293,970 B1 | 9/2001 | Wolfinbarger et al. | |
| 6,544,289 B2 | 4/2003 | Wolfinbarger et al. | |
| 6,569,200 B2 | 5/2003 | Wolfinbarger et al. | |
| 6,734,018 B2 | 5/2004 | Wolfinbarger et al. | |
| 6,743,574 B1 | 6/2004 | Wolfinbarger et al. | |
| 7,063,726 B2 | 6/2006 | Crouch et al. | |
| 7,338,757 B2 | 3/2008 | Wolfinbarger et al. | |
| 8,563,232 B2 | 10/2013 | Wolfinbarger et al. | |
| 8,574,826 B2 | 11/2013 | Wolfinbarger et al. | |
| 11,058,530 B2 | 7/2021 | Chen et al. | |
| 2001/0018614 A1 | 8/2001 | Bianchi | |
| 2002/0103542 A1 | 8/2002 | Bilbo | |
| 2003/0093152 A1 | 5/2003 | Pedersen et al. | |
| 2004/0260315 A1* | 12/2004 | Dell | A61F 2/0063 623/23.72 |
| 2007/0250164 A1 | 10/2007 | Troxel | |
| 2008/0097601 A1 | 4/2008 | Cordori-Hurff et al. | |
| 2008/0125871 A1 | 5/2008 | Fard | |
| 2009/0082864 A1 | 3/2009 | Chen et al. | |
| 2010/0030340 A1 | 2/2010 | Wolfinbarger et al. | |
| 2010/0145451 A1 | 6/2010 | Dee | |
| 2011/0015757 A1 | 1/2011 | Wolfinbarger et al. | |
| 2011/0022171 A1 | 1/2011 | Richter et al. | |
| 2011/0251602 A1 | 10/2011 | Anderson et al. | |
| 2012/0158134 A1 | 6/2012 | Codori-Hurff et al. | |
| 2013/0184722 A1 | 7/2013 | Stopek et al. | |
| 2013/0218294 A1 | 8/2013 | Wolfinbarger et al. | |
| 2014/0065238 A1 | 3/2014 | Wolfinbarger et al. | |
| 2014/0154663 A1 | 6/2014 | Wolfinbarger et al. | |
| 2014/0180437 A1 | 6/2014 | Wolfinbarger et al. | |
| 2014/0257517 A1 | 9/2014 | Deichmann et al. | |
| 2015/0209128 A1 | 7/2015 | Markman | |
| 2015/0250582 A1 | 9/2015 | Greenhalgh et al. | |
| 2016/0256259 A1 | 9/2016 | Wirth et al. | |

OTHER PUBLICATIONS

Canadian Office Action for Canadian Application No. 2,970,965, dated Mar. 7, 2018, 4 pages.
Canadian Examination Report for Canadian Application No. 3,041,872, dated May 6, 2020, 5 pages.
Extended European Search Report for European Application No. 16 856 276.7, dated May 21, 2019, 10 pages.
International Search Report and Written Opinion for International Application PCT/US2016/057038, dated Feb. 24, 2017—11 Pages.
International Preliminary Report on Patentability and Written Opinion for International Application No. PCT/US2016/057038, issued Apr. 17, 2018, 8 pages.
Entire patent prosecution history of U.S. Appl. No. 15/534,237, filed Jun. 8, 2017, entitled, "Soft Tissue Grafts, and Methods of Making and Using Same."

* cited by examiner

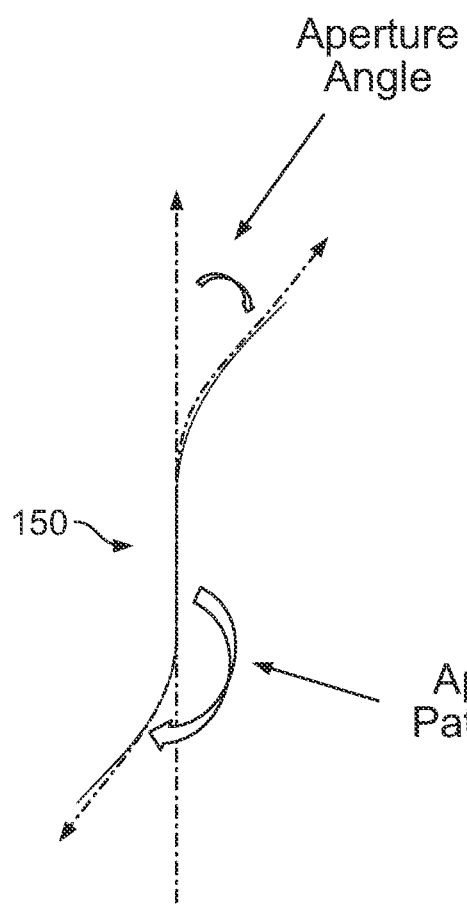
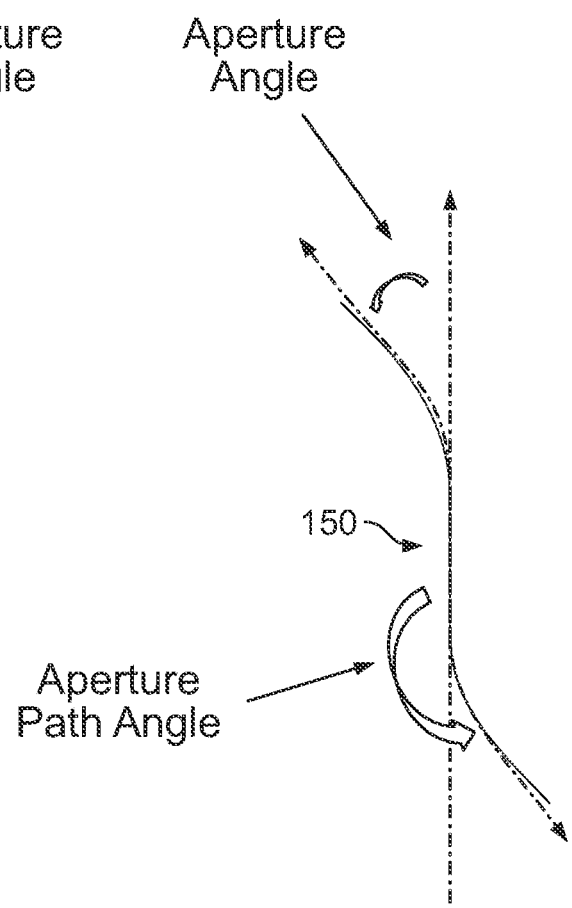
FIG. 4C
FIG. 4D

SOFT TISSUE GRAFTS, AND METHODS OF MAKING AND USING SAME

CROSS-REFERENCE TO RELATED APPLICATIONS

This Application is a Continuation of Ser. No. 15/534,237 filed Jun. 8, 2017, which is a U.S. National Phase Application Of PCT International Application PCT/US2016/ 057038, filed Oct. 14, 2016, which claims priority to U.S. Patent Application No. 62/242,930, filed Oct. 16, 2015, and U.S. Patent Application No. 62/257,582, filed Nov. 19, 2015, the contents of each of which are incorporated herein by reference in their entirety.

TECHNICAL FIELD

The present invention relates to soft tissue grafts, methods of preparing soft tissue grafts, and methods of use thereof. The present invention also relates to soft tissue grafts for use in mastopexy or breast reconstruction procedures. The present invention also relates to soft tissue grafts for use in rotator cuff repair or reinforcement. The present invention also relates to soft tissue grafts for use in tendon and ligament repair.

BACKGROUND

A wide variety of soft tissue products are used in medical, surgical, veterinary, and other applications. These soft tissue products can be used in load-bearing and non-load bearing applications and can be supplied in a variety of forms. The intended use of the soft tissue product may dictate certain aspects of its form such as size, shape, or thickness. General soft tissue grafts, however, may be unable to meet desired dimensions, or may require substantial modification before they are suitable for a particular use.

SUMMARY

Soft tissue grafts, packaged soft tissue grafts, and methods of making and using soft tissue grafts are disclosed.

In one example, a soft tissue graft is disclosed. The soft tissue graft includes processed tissue material having first and second opposed surfaces. The first and second opposed surfaces are bounded by first and second edges. The first edge has a concave shape that curves toward the second edge. The second edge has a convex shape that curves away from the first edge. The first surface comprises a plurality of apertures. At least one of the apertures is formed from a multi-directional separation in the first surface.

In another example, another soft tissue graft is disclosed. The soft tissue graft includes processed tissue material having first and second opposed surfaces. The processed tissue material has a trapezoidal shape with a pair of parallel edges. The first surface comprises a plurality of first apertures.

In yet another example, another soft tissue graft is disclosed. The soft tissue graft includes processed tissue material having first and second opposed surfaces. The first and second opposed surfaces are bounded by first and second edges. The first edge has a concave shape that curves toward the second edge. The second edge has a convex shape that curves away from the first edge. The first surface is meshed to form a plurality of apertures with a predetermined density.

In still another example, a packaged soft tissue graft is disclosed. The packaged soft tissue graft includes a support, processed tissue material, and packaging material. The support has a base and a projection extending upward from the base. The processed tissue material has first and second opposed surfaces. The processed tissue material is positioned to cover at least a portion of the projection with the first surface facing away from the projection and the second surface facing the projection. The first surface comprises a plurality of apertures. The packaging material encloses the support and the processed tissue material.

In yet another example, another packaged soft tissue graft is disclosed. The packaged soft tissue graft includes a support, processed tissue material, a frame, and packaging material. The processed tissue material has first and second opposed surfaces. The processed tissue material is positioned to cover at least a portion of the support with the first surface facing away from the support and the second surface facing the support. The first surface comprises a plurality of apertures. The frame is configured to surround the processed tissue material and press edges of the processed tissue material against the support. The frame is configured to apply a tension to the processed tissue material when the processed tissue material is positioned between the support and the frame. The packaging material encloses the support, the frame, and the processed tissue material.

In still another example, a method of making a soft tissue graft is disclosed. The method includes positioning a cutting die on a surface of tissue material, pressing the cutting die into the tissue material to cut the tissue material, and processing the cut tissue material to create processed tissue material.

BRIEF DESCRIPTION OF THE DRAWINGS

The drawing figures depict one or more implementations in accord with the present concepts, by way of example only, not by way of limitations. In the figures, like reference numerals refer to the same or similar elements.

FIGS. 4A-4D show measurements of apertures for soft tissue grafts.

DETAILED DESCRIPTION

Figure 1:
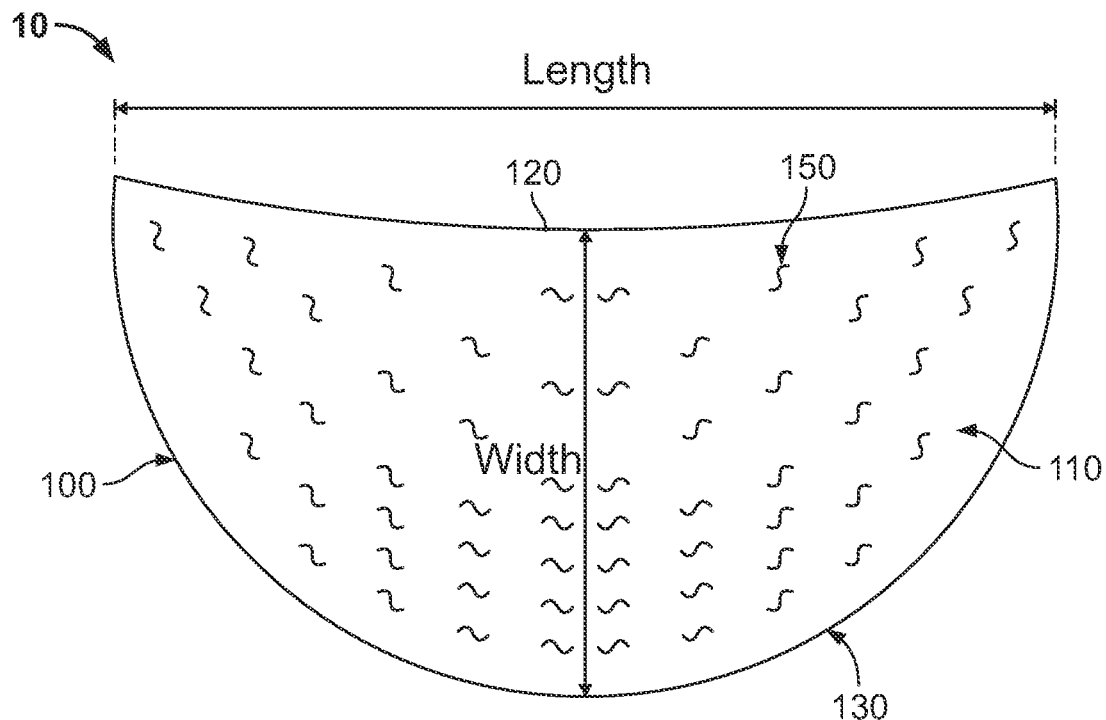
FIG. 1 shows an example of a soft tissue graft.

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

The detailed description below and the accompanying drawings disclose examples of soft tissue grafts and methods of making and using soft tissue grafts. The examples of soft tissue grafts have sizes, shapes, and thicknesses selected for particular uses. The examples of soft tissue grafts may further include apertures to promote successful implantation. The soft tissue grafts may be packaged or unpackaged.

The examples discussed below may be particularly suitable for use in mastopexy or breast reconstruction procedures. Mastopexy, or breast lift, is a procedure designed to improve the appearance of sagging or ptotic breasts. For example, one goal of the surgery is to improve the shape and position of the breast while minimizing visible scars. Breast reconstruction is a procedure used to restore form and function after mastectomy. The goals of implant-based breast reconstruction include: recreation of the breast mound-including defining the contour of the lower pole to reestablish normal ptosis and the creation of aesthetically pleasing inframammary fold. Various procedures and modifications of mastopexy are known in the art.

The examples discussed below may be particularly suitable for rotator cuff repair or reinforcement, tendon and ligament repair or reinforcement, and/or capsular reconstruction. Rotator cuff repair or reinforcement is a procedure to restore normal form, function, and range of motion to a patient's shoulder following partial or complete tear of the patient's rotator cuff. Tendon and ligament repair are procedures for remedying partial or complete tears of a patient's ligaments or tendons. Use of the example grafts in rotator cuff repair can restore stability of the shoulder joint and resolve dysfunction and pain. Capsular reconstruction is a procedure to recreate the joint capsule thereby restoring normal joint biomechanics and stability. The implanted graft has a high ultimate load and suture retention strength. Soft tissue repairs augmented with the graft may demonstrate improved strength, reduce re-tear and improved clinical outcomes. Moreover, repair of complete and chronic tendon tears with the graft supplements inadequate tendon tissue. Tendon augmentation can provide a more effective treatment of chronic or acute conditions by creating a stronger repair construct. A stronger repair may allow for more aggressive rehabilitation decreasing postoperative stiffness, muscle atrophy, and repair site gapping.

Examples discussed below and shown in the drawings improve over the art by providing a suitable size, shape, and thickness for a predetermined procedure, thereby eliminating the need for substantial processing or cutting of the graft prior to implantation. Additionally, the examples discussed below may include apertures to provide increased locations for angiogenesis (formation of blood vessels), as well as improved tissue ingrowth following implantation, thereby speeding the post-implantation healing process.

In preparation of the example grafts below, soft tissue can be cut in such a way that allows for suturing zones on the graft without adversely impacting the biomechanical strength of the graft, and without impacting the placement of apertures in the soft tissue. The processes described below are designed to minimize introduction of bio-burden during the process of forming the soft tissue graft. The final soft tissue grafts allow for intra-operative suturing at an edge of the graft, while eliminating risk of pull-out of sutures through apertures in the graft.

The examples described below have a shape designed for minimum graft size necessary to achieve desired intraoperative coverage. These examples support the use of smaller grafts to achieve existing procedural techniques, potentially saving institutions cost and shelf space. In some examples, a concave shape is provided that roughly mirrors natural borders of pectoralis major muscle aiding in various reconstructive techniques, potentially minimizing trauma to the pectoralis major muscle. Some examples are designed to allow for fat grafting around the upper pole, for enhanced aesthetic outcomes without impacting aperture placement and/or ability of the graft to enable fluid egress. Some examples have different zones of elongation, in order to maximize fluid egress in 3D planes in high risk areas while at the same time providing defined elongation in north-south plane.

The concave design of certain examples allows for maximum utilization of tissue, minimizing wastage of donated tissue. The concave shape allows for intra-operative shape adjustment based on patient requirements/physiology. The processes described below promote uniform and consistent handling of soft tissue to enhance pre-operative planning and provide a pathway to technical training to less experienced surgeons.

The example soft tissue grafts described below may include apertures. The apertures are designed to minimize stress concentrations in the soft tissue. The apertures may minimize the number of drains used post-operatively. The apertures may further maximize post-operative incorporation and revascularization of the graft. In some examples, linear apertures are used, which close when the tissue tensioned parallel to the apertures and open when tensioned obliquely or orthogonally to the apertures, to increase the potential vascular pathways necessary for maximum tissue remodeling and regeneration. These examples could lead to earlier structural integrity of the graft due to the increased vascular channels, resulting in more rapid granulated tissue and tissue ingrowth.

In some examples, apertures may be oriented to create variable zones of fluid egress through the soft tissue graft corresponding to anatomical zones. Apertures may be patterned to create consistent 2D openings in the 3D anatomical space where utilized. Minimizing the potential gapping or closing of the aperture maximizes the contact between ADM and implant, while minimizing potential dead space leading to post-operative complications. Apertures may be sized to maximize opening when placed over an implant, and may be shaped for optimal opening when tensioned in three dimensions.

In some examples, the soft tissue grafts are meshed. The meshing pattern maximizes the opening area of the soft tissue graft while maintaining biomechanical integrity through suture borders and internal graft bands. The meshing pattern may be designed to enhance current and contemplated techniques in breast reconstruction. The meshing pattern may also be designed to provide controlled/defined expansion in any surgical plane.

While the following examples are described chiefly with respect to particular procedures (such as mastopexy, breast reconstruction, rotator cuff repair, tendon/ligament reconstruction, or capsular reconstruction), it should be readily apparent that the examples herein are not so limited. The following examples and variations thereof may alternatively be used in any number of procedures requiring the use of a soft tissue grafts. Other suitable procedures will be apparent from the description herein.

Definitions are set forth below to provide a clear and consistent understanding of the specification and claims, including the scope to be given such terms.

And/or. It should be understood that the use of "and/or" is defined inclusively such that the term "a, b and/or c" should be read to include all the combination of a, b, and c, including "a, b, and c," "a and b," "a and c," "b and c," "a, b, or c," "a or b," "a or c," "b or c," "a," "b," and "c." hole Aperture. The term "aperture" as used herein is intended to encompass any separation in a surface of the soft tissue, including holes, slits, cavities, voids, fenestrations, channels, or other types of openings, regardless of whether that separation extends part of the way or all of the way through the soft tissue.

Biocompatible. The term "biocompatible" as used herein is intended to encompass any material which does not provoke an adverse response in a patient. For example, a suitable biocompatible material when introduced into a patient does not itself provoke a significant immune response, and is not toxic to the patient.

Biomechanical strength. The term "biomechanical strength" as used herein is intended to encompass those properties exhibited by a tissue graft, including loading strength, compressive strength, and tensile strength.

Impregnating. The term "impregnating" as used herein is intended to encompass any processing conditions which result in filling the internal matrix of a graft with an identified material.

Internal matrix. The term "internal matrix" as used herein is intended to encompass the intercellular substance of such soft tissue including for example ligaments and tendons, including collagen and elastin fibers and base matrix substances.

Plasticizer. The term "plasticizer" as used herein is intended to encompass any biocompatible compounds which can easily displace/replace water at the molecular level and preferably have a low molecular weight such that the plasticizer fits into the spaces available to water within the molecular structure of the bone or soft tissue. Such plasticizers are preferably not toxic to the cellular elements of tissue into which the graft is to be placed. Suitable plasticizers are described in U.S. Pat. No. 6,569,200, the contents of which are incorporated herein by reference in their entirety.

Processed tissue material. The term "processed tissue material" as used herein is intended to encompass native, normal tissue that has been procured from an animal source (e.g. human or non-human, such as bovine, porcine, canine including, but not limited to, a dog, equine, ovine, or non-human primate including, but not limited to, ape and gorilla, in origin), preferably a mammal, and mechanically cleaned of attendant tissues and/or chemically cleaned of cells and cellular debris.

Soft tissue graft. The term "soft tissue graft" as used herein is intended to encompass load-bearing and non-load-bearing soft tissue products composed of an internal matrix which includes collagen, elastin, and high molecular weight solutes which during cleaning may be removed.

The soft tissue grafts disclosed herein may be derived from allogenic, autogenic, or xenogenic sources. The tissue material used for the grafts may be processed from human or animal tissue. In one aspect, the processed tissue material may be derived from native tissues, such as stomach, intestine, dermis, fascia lata, pericardium, bladder, and dura mater. The processed tissue material may be, for example, biologically-derived collagenous materials, such as the intestinal submucosa described in U.S. Patent Application Publication Nos. 2002/0103542 and 2008/0097601, each of which are incorporated by reference in their entirety. When implanted into a mammalian patient, the processed tissue material may undergo controlled biodegradation occurring with adequate living cell replacement such that the original implanted graft is remodeled by the patient's living cells, and, in some examples, the graft does not interfere with radiographic imaging.

In another aspect, the processed tissue material described herein consists essentially of and/or consists of the one or more soft tissue(s); and a liquid, solution, or solvent. In some examples, the processed tissue material consists essentially of and/or consists of components from the one or more soft tissue(s). The term "essentially consisting of" defines the scope of the processed tissue material to include additional elements that do not materially affect the porosity or void fraction of the processed tissue material consisting of initial elements. For example, the processed tissue material consisting essentially of one or more soft tissue(s) may include elements in addition to the one or more soft tissue(s) that do not materially affect the extracellular matrix composition of the processed tissue material consisting of the one or more soft tissue(s).

Reference now is made in detail to the examples illustrated in the accompanying drawings and discussed below. FIGS. 1 and 2A-2C illustrate an example of a soft tissue graft 10. Soft tissue graft 10 is formed from processed tissue material 100. Details regarding soft tissue graft 10 are set forth below.

In one example, processed tissue material 100 may be dermis, and the processed tissue material may comprise a reticular lamina layer. In additional examples, the processed tissue material 100 comprises a basal lamina layer and a reticular lamina layer, and the processed tissue material 100 may comprise a basal lamina layer, a reticular lamina layer, and adipose tissue. In further examples, the processed tissue material 100 may exclude a basal lamina layer, a reticular lamina layer, and/or adipose tissue. The processed tissue material 100 may have one, two, three, or all sides on which the reticular lamina layer is exposed. For example, when the processed tissue material 100 consists of the reticular lamina layer, all sides of such a processed tissue material would be reticular sides. When at least 60, 70, 80, 90, 95, 98, 99 or 100% of a side of a material is composed of the reticular lamina layer, such a side may be called a reticular side, and one, two, three or all sides of processed tissue material 100 may be reticular sides. In some examples, processed tissue material 100 may have top and bottom reticular sides.

As shown in FIG. 1, processed tissue material 100 has a first major surface 110 and a second surface (not shown) opposite the first surface. Surface 110 is bounded by edges 120 and 130. Edge 120 has a concave shape that curves toward edge 130, and edge 130 has a convex shape that curves away from edge 120. The radius of curvature of edge 120 is longer than the radius of curvature of edge 130. Edges 120 and 130 share both ends; in other words, edges 120 and 130 start and end at the same points. As shown in FIG. 1, processed tissue material 100 is symmetrical about a line bisecting edges 120 and 130. Processed tissue material 100 may be symmetrical about one or multiple different lines dependent on the intended use of graft 10.

FIG. 1 shows lines representing the length and width of processed tissue material 100. Length may be measured from the most distant points of processed tissue material 100, with width measured from the most distant points of processed tissue material 100 along a line orthogonal to length. Processed tissue material 100 may have a length of from 5, 6, 7, 8, 9, 10, 13 or 15 cm to 20, 23, 25, 27 or 30 cm. Processed tissue material 100 may have a width of from 2, 5, 6, 7, 8, 9, 10 or 15 cm to 15, 20, 21, 22, 23, 24, 25 or 30 cm. Processed tissue material 100 may have a thickness (measured from surface 110 to the opposing surface) in a range of from 0.1 mm to 10 mm. Processed tissue material 100 may have an average thickness of from 0.05, 0.1, 0.5, 1, 2, 3, 4, 5 or 6 mm to 6, 7, 8, 9, 10, 11, 12, 13, 15, or 20 mm. The thickness of processed tissue material 100 need not be uniform and may increase at locations closer to edges 120 and 130 of processed tissue material 100.

As set forth above, edges 120 and 130 may have different radii of curvature. Concave edge 120 may have a radius of curvature of from 25 cm to 50 cm, and more preferably, from 30 cm to 46 cm. Convex edge 130 may have a radius of curvature of from 5 cm to 15 cm, and more preferably, from 6.5 cm to 10.6 cm.

The shape and size of processed tissue material 100 shown in FIG. 1 is selected to be suitable for a mastopexy or breast reconstruction procedure. The shape may facilitate the performance of these procedures by requiring little or no pre-surgical modification (such as cutting). It will be understood that other shapes for processed tissue material 100 may be selected based on the intended procedure. Examples of possible shapes include, for example, circles, semicircles, partial circles, ellipses, triangles, rectangles, trapezoids, parallelograms, squares, other regular or irregular, convex or concave polygons, or combinations of these shapes. A concave polygon is defined as a polygon with one or more interior angles greater than 180°, and a convex polygon is defined as a polygon with all its interior angles less than 180°. In some examples, the edges of the processed tissue material may be curved, so as to form a continuous edge lacking any corners or vertices. In additional examples, the concave border curves toward the convex border, and the convex border curves away from the concave border. Additionally, it will be understood that processed tissue material 100 need not be symmetrical, but may have asymmetrical features in order to correspond to variations in the anatomy of the intended recipient (such as left/right variations). For one example, as shown in FIG. 1, processed tissue material 100 may have apertures of one shape (such as an S-shape) on a right side of the graft, and apertures of a mirrored shape (such as a mirror S-shape) on a left side of the graft.

In the example shown in FIG. 1, the surface 110 of processed tissue material 100 includes a number of apertures 150. Apertures 150 may extend all of the way through processed tissue material 100, or may extend only part of the way through processed tissue material 100.

Apertures 150 may be formed from cutting into surface 110 of processed tissue material 100, or may be formed from removing at least a part of processed tissue material 100 from surface 110. The cutting of apertures 150 in surface 110 may be performed, for example, with a knife, blade, scissors, press, pressurized fluid or pellet, or a laser. For example, the blade may be a scalpel blade (e.g. steel or diamond or other material), electronic scalpel or harmonic scalpel or steel rule die or machined cutting die blade that is pressed into the skin. A water jet or dry ice blaster, liquid or pellet pressurized to a small area may also be used to cut the tissue. Examples of the lasers include femtosecond laser and epilog laser, and other examples will be apparent to those skilled in the art.

Apertures 150 may each have the same shape and size, or may have different shapes and sizes. Where the shapes and/or sizes of apertures 150 differ, the differences may be based on the location of the aperture 150 on processed tissue material 100.

The shape, size, and density of apertures is selected to promote angiogenesis and vascularization of the soft tissue graft following implantation, without adversely affecting a biomechanical strength of the graft. Examples of shapes, sizes, and layouts of apertures 150 are set forth below.

Figure 3A:
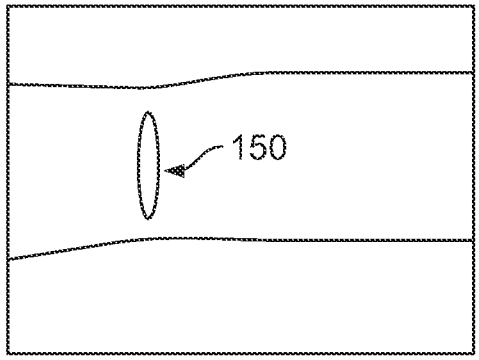
FIGS. 3A-3F show examples of different aperture shapes for soft tissue grafts.
Figure 3B:
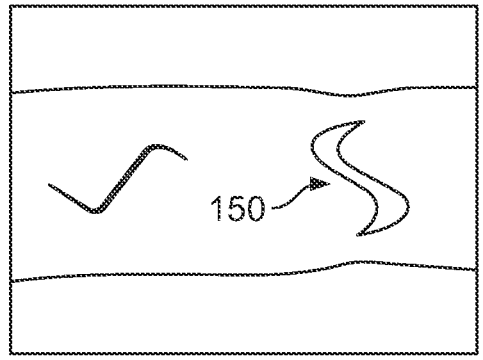
Figure 3C:
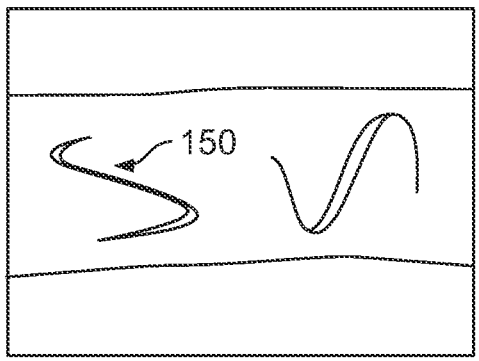
Figure 3D:
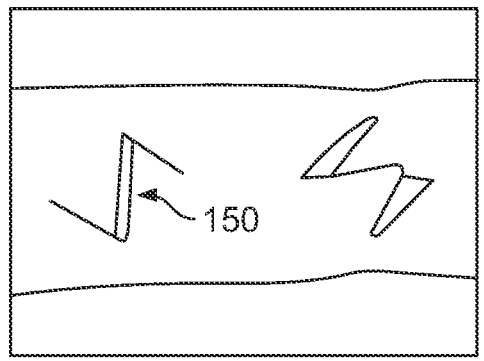
Figure 3E:
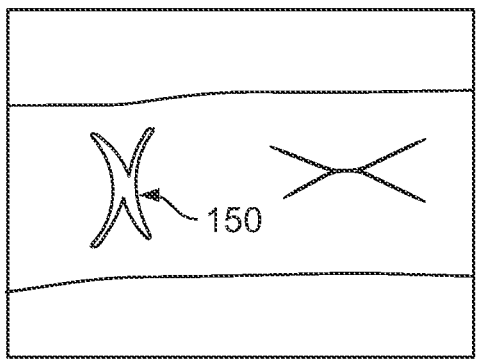
Figure 3F:
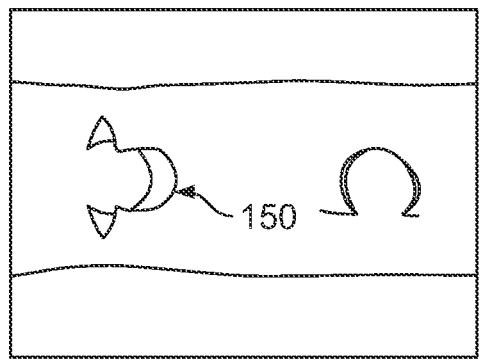

FIGS. 3A-3F show various possible shapes for apertures 150. As shown in FIG. 3A, apertures 150 may be formed from a linear separation or cut in surface 110. Alternatively, apertures 150 may be formed from a multi-directional separation or cut in surface 110. As used herein, the term "multi-directional" refers to a separation that extends in more than one different direction. The multi-directional separation may be arc-shaped, or may have another shape. Possible shapes for the multi-directional separation include S-shapes (as shown in FIGS. 3B and 3C), Z-shapes (as shown in FIG. 3D), J-shapes, L-shapes, X-shapes (as shown in FIG. 3E), omega shapes (as shown in FIG. 3F), or mirror images thereof. In additional examples, the multi-directional separation may have two, three, four, five, six or more and/or three, four, five, six, seven or fewer directions.

Figure 4A:
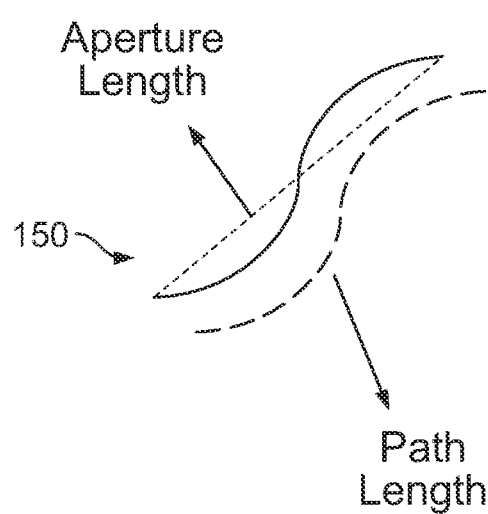

The length of each aperture may be considered to be the distance between opposite ends of the aperture, without consideration of the particular path of the aperture (in the case of multi-directional separations). FIG. 4A shows an example of a length measurement for an S-shaped aperture. An average length of the apertures 150 may be from 0.3, 0.4, 0.5, 0.6, 0.7 or 0.8, 2, 4, 6 or 8 mm to 10, 20, 25, 28, 30, 35 or 40 mm. Apertures 150 may each have a length in a range of from 1 mm to 10 mm.

Figure 4B:
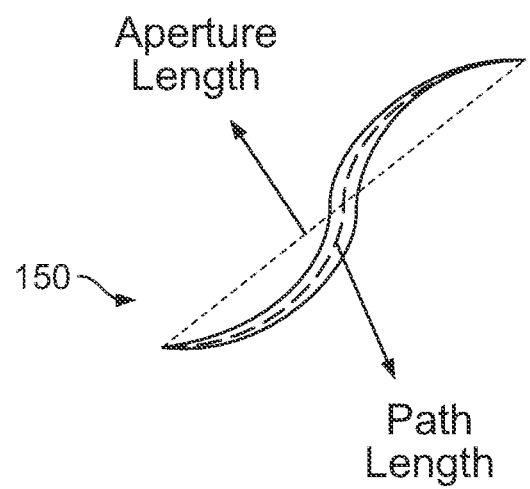

In addition to aperture length, multi-directional apertures may be characterized by a path length of the aperture, i.e., a length along the particular path or cut of the aperture. FIG. 4B shows an example of a path length measurement for an S-shaped aperture. An average path length of multi-directional apertures 150 may be from 0.3, 0.4, 0.5, 0.6, 0.7 or 0.8, 2, 4, 6 or 8 mm to 10, 20, 25, 28, 30, 35 or 40 mm.

As shown in FIGS. 4A and 4B, a multi-directional aperture will have a path length which is longer than the aperture length. The ratio of aperture length to path length for the multi-directional apertures may be 0.2, 0.3, 0.4, 0.5, 0.6, 0.7, 0.8, 0.9, 0.95, or 0.99 or more and/or less than 1.0, 0.99, 0.95, 0.9, 0.8, 0.7, 0.6, of 0.5.

In addition to aperture length and path length, multi-directional apertures may also be characterized by an aperture angle, i.e., an angle between a central portion of the aperture and end portions of the aperture, or a aperture path angle, i.e., an angle between one portion of the aperture path and another portion of the aperture path. FIGS. 4C and 4D show an example of an angle measurement for an S-shaped aperture and a mirror S-shaped aperture, respectively. Average path angles may be independently from −300, −200, −100, −50, −10 or −5 degrees to 5, 10, 50, 100, 200 or 300 degrees.

Adjacent apertures 150 may be spaced apart at a distance of from 0.5 mm to 30 mm. The aperture length and spacing may be selected such that the ratio of average distance between adjacent apertures to average length of apertures is from 0.5, 0.6, 0.7, 0.8, 0.9, 0.95, or 0.99 or more and/or less than 1.0, 0.99, 0.95, 0.9, 0.8, 0.7, or 0.6. In some examples, this ratio may be from 0.2 to 0.99, from 0.3 to 0.9, from 0.5 to 0.8, or from 0.6 to 0.8.

Alternative or additionally, apertures 150 may be characterized by the area created by the aperture with or without stretching of the processed tissue material. It will be understood that when the aperture is formed by cutting the tissue material without removing any part of the tissue material, the size of the aperture is zero prior to any stretching of the processed tissue material. When the aperture is formed by removing tissue material, the aperture may have an area even without stretching of the processed tissue material. An average area of apertures 150 formed in processed tissue material 100 may be from 0, 0.1, 0.4, 0.5, 1, 5, 8 or 10 mm$^2$ to 50, 100, 150, 180 or 200 mm$^2$. Apertures 150 may all have an area in a range of from 0.5 mm$^2$ to 200 mm$^2$.

The positioning and density of apertures 150 on processed tissue material 100 may be uniform across surface 110, or may vary. Apertures may be arrayed on surface 110 in rows and/or columns, or may be randomly dispersed on surface 110.

In one example, apertures 150 are more concentrated in the center of surface 110. In this example, surface 110 has a central region which may be considered to be the portion of surface 110 closer to a line bisecting edges 120 and 130 than the ends of edges 120 and 130. The number and/or density of apertures 150 in the central region of surface 110 is greater than the number and/or density of apertures in the remaining area of surface 110.

In another example, apertures 150 are more concentrated in the lower region of surface 110. In this example, surface 110 has a lower region which may be considered to be the portion of surface 110 closer to edge 130 than edge 120. The number and/or density of apertures 150 in the lower region of surface 110 is greater than the number and/or density of apertures in the remaining area of surface 110.

Figure 2A:
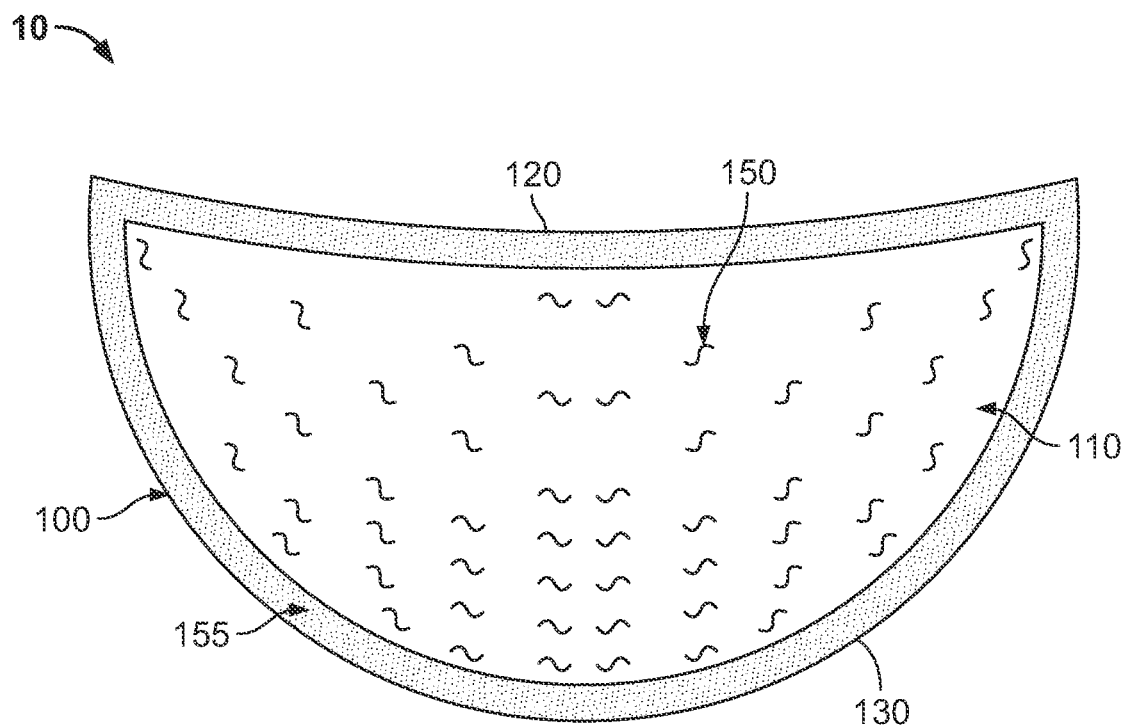
FIGS. 2A-2C show examples of variations in aperture layout of the soft tissue graft of FIG. 1.

As shown in FIG. 2A, apertures 150 may not be positioned close to the edges of surface 110. In one example, no apertures are positioned within a predetermined distance from edges 120 and 130. The predetermined distance may be, for example, at least 0.5, 1.0, 1.2, 1.5, 2.0, 2.5, 3.0 or 3.5 cm. Providing an aperture-free space along the edges of surface 110 may be desirable in order to create a suture zone 155, e.g., a zone for steady and secure suturing of graft 10 during implantation.

Figure 2B:
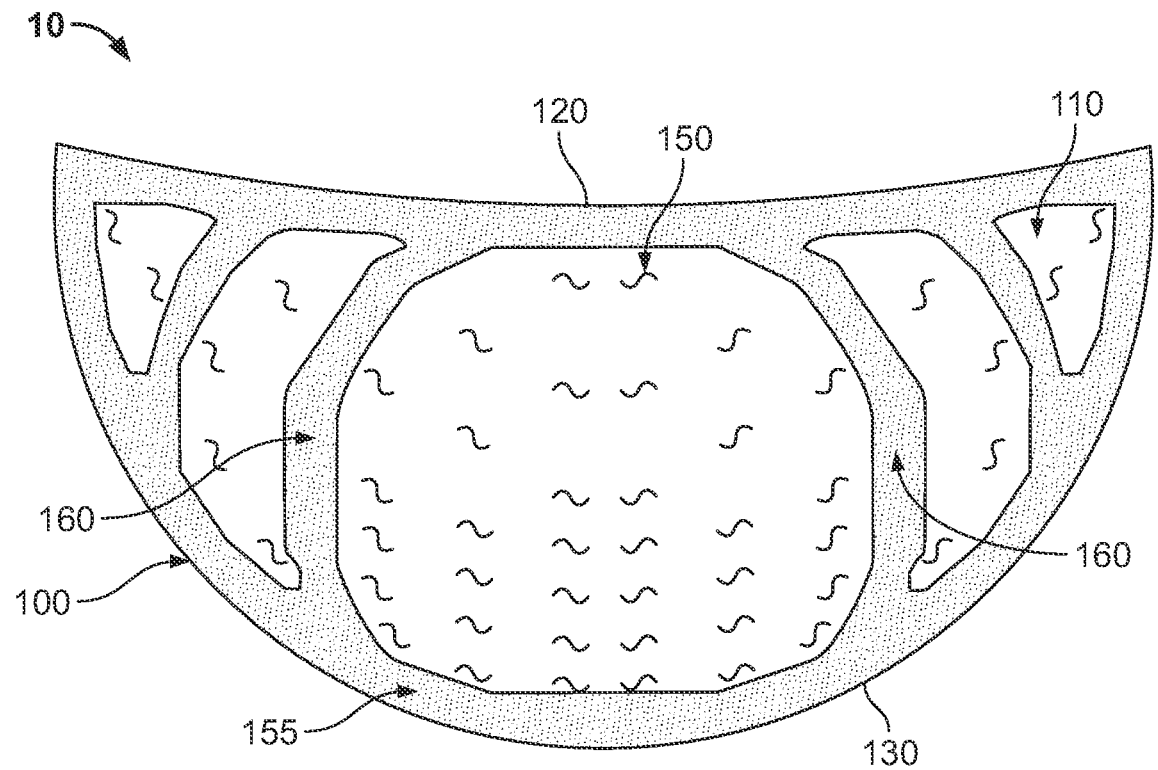
Figure 2C:
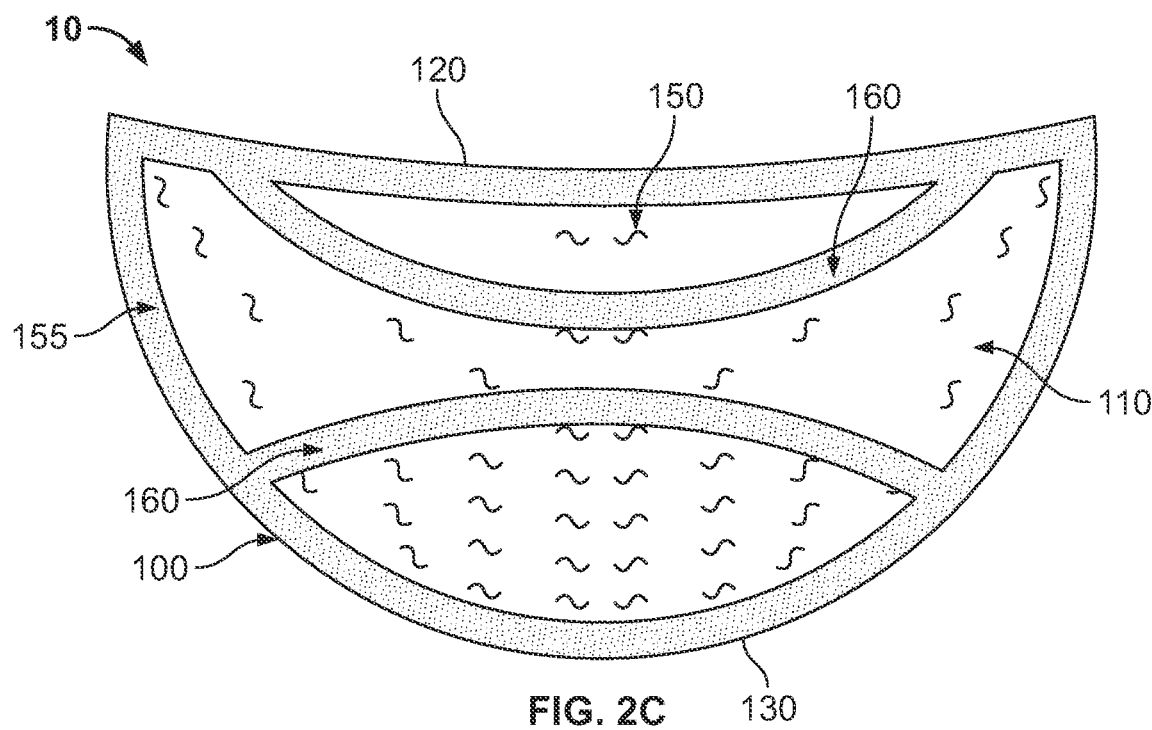

As shown in FIG. 2B, surface 110 may also include one or more bands 160 which are free from apertures 150. Bands 160 may be located along the edges of processed tissue material 100, or may extend across a portion of processed tissue material 100, with apertures 150 provided on each side of the band 160. Bands 160 may have a width of at least 0.5, 1.0, 1.2, 1.5, 2.0, 2.5, 3.0 or 3.5 cm, for example. In one example, a band 160 extends from edge 120 to edge 130 of processed tissue material 100, as shown in FIG. 2B. In another example, a band 160 extends from one portion of edge 120 to another portion of edge 120, and/or from one portion of edge 130 to another portion of edge 130, as shown in FIG. 2C. Bands 160 may be straight or curved. In the example shown in FIG. 2B, multiple convex bands 160 which extend from edge 120 to edge 130, and which curve away from a center of processed tissue material 100, are provided. Providing bands 160 in this layout may maintain a biomechanical strength of graft 10 during or after implantation.

Processed tissue material 100 of graft 10 has been processed to be suitable for implantation. Such processing may include cleaning the tissue material, disinfecting the tissue material, skiving the tissue material to a predetermined thickness, removing cellular elements and small molecular weight solutes from the tissue material (i.e. "decellularizing" the tissue material), plasticizing the tissue material, packaging the tissue material, and/or sterilizing the tissue material. During plasticization, the internal matrix of the tissue material is impregnated with one or more plasticizers.

FIGS. 5A-5D illustrate an example of a packaged soft tissue graft 200. The packaged soft tissue graft 200 includes processed tissue material 210, a support 220, and packaging material 240. Processed tissue material 210 may be any processed tissue material described above with respect to processed tissue material 100. Additional details regarding packaged soft tissue graft 200 are set forth below.

Support 220 supports processed tissue material 210. Support 220 is formed from a rigid, semi-rigid, flexible, porous, and/or spongy material in order to prevent folding, twisting, or flexing of processed tissue material 210 after packaging. Support 220 may be formed from a rigid biocompatible polymer, or may be covered with a biocompatible material, in order to prevent possible adverse reaction following implantation of processed tissue material 210. Suitable biocompatible materials for use as support 220 include, for example, metals such as stainless steel or foil, plastic such as polyethylene, polyester, or acrylonitrile-butadiene-styrene (ABS), polytetrafluoroethylene (PTFE), ceramics such as aluminum oxide, or natural materials as cellulose sponge, or combinations of the foregoing materials, such as PET/AlO. Other suitable biocompatible materials will be apparent to those of skill in the art.

Support 220 may be formed, for example, by injection molding, vacuum forming, or three-dimensional printing. In one example, the size of support 220 is tailored to the dimensions of the patient that will be receiving the soft tissue graft. In this example, the area of the patient to receive the soft tissue graft may be measured, and those measurements may be used to calculate the size of support 220. Support 220 may then be three-dimensional printed according to the desired dimensions. This example may be helpful in order to model the intra-operative positioning of the soft tissue graft prior to implantation, while the processed tissue material is packaged.

Figure 5A:
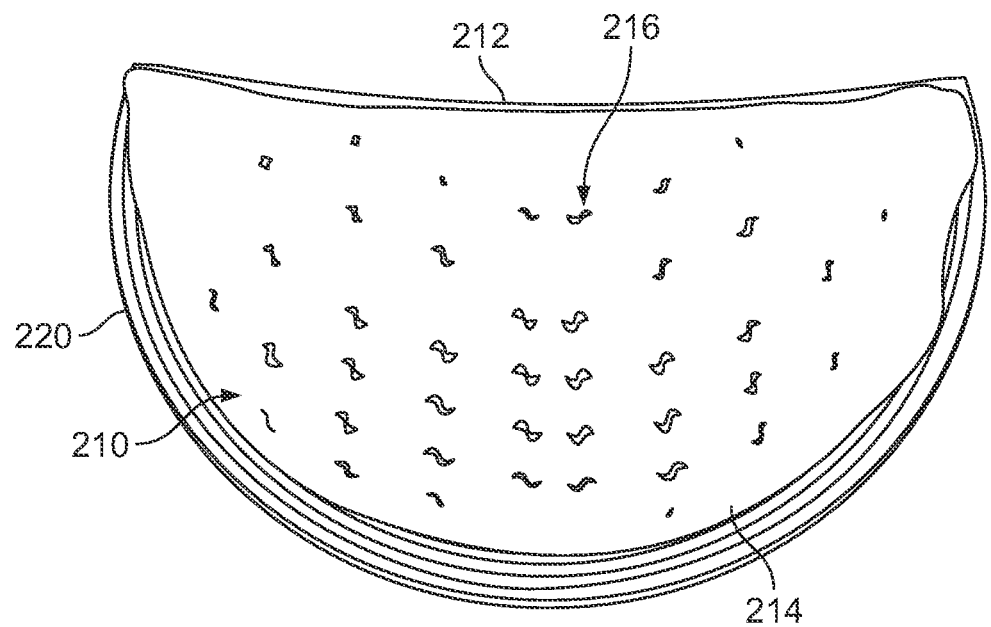
FIGS. 5A-5D show an example of a packaged soft tissue graft.
Figure 5B:
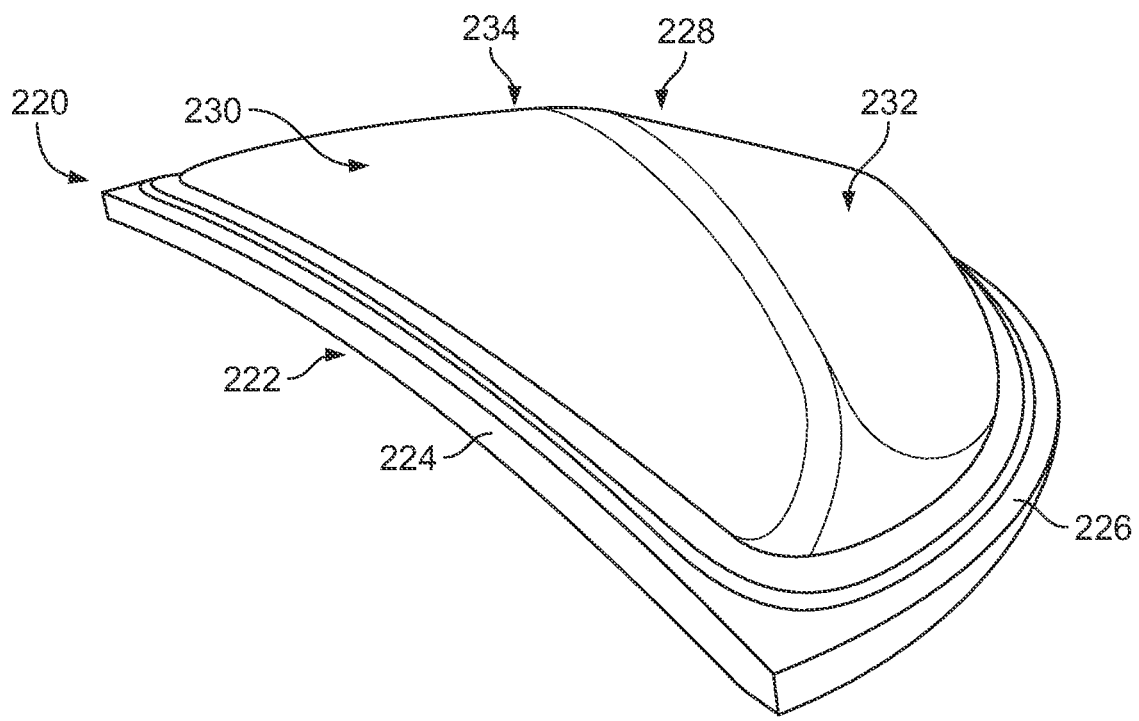

As shown in FIGS. 5A and 5B, support 220 may include a base 222 and a projection 228 extending upward from the base. Base 222 has a flat lower surface so support 220 can sit stably on a shelf or surface. Base 222 may have a shape matching corresponding to a shape of processed tissue material 210. As shown in the example of FIG. 5A, processed tissue material has edges 212 and 214. Edge 212 has a concave shape that curves toward edge 214, and edge 214 has a convex shape that curves away from edge 212. Likewise, base 222 has edges 224 and 226 which correspond in shape to edges 212 and 214 of processed tissue material 210.

Projection 228 enables processed tissue material 210 to be maintained in a three-dimensional form in the packaging. The shape or contour of projection 228 may be selected to correspond the shape or contour which processed tissue material 210 is intended to take following implantation, so that processed tissue material 210 can be stored and/or maintained in its intended position for implantation. Support 220 and/or projection 228 may thus be designed to assist in simulating an intraoperative appearance of processed tissue material 210, in order to promote ease of use of the packaged soft tissue graft 200.

Projection 228 may be formed from one uniform surface, such as a dome, or partial sphere, or may be formed from multiple surfaces. In one example, as shown in FIG. 5B, projection 228 includes first and second support surfaces 230 and 232. Surfaces 230 and 232 define a ridge 234 extending between them. Ridge 234 extends from base 222 over the top of projection 228 and back down to base 222. Processed tissue material 210 covers at least a portion of both surfaces 230 and 232 and ridge 234.

While support 220 is illustrated as having a projection 228, it will be understood that this is not intended to be limited. In another example, a flat, two-dimensional support may be used, such as when a three-dimensional positioning of processed tissue material 210 is not anticipated during implantation.

Figure 5C:
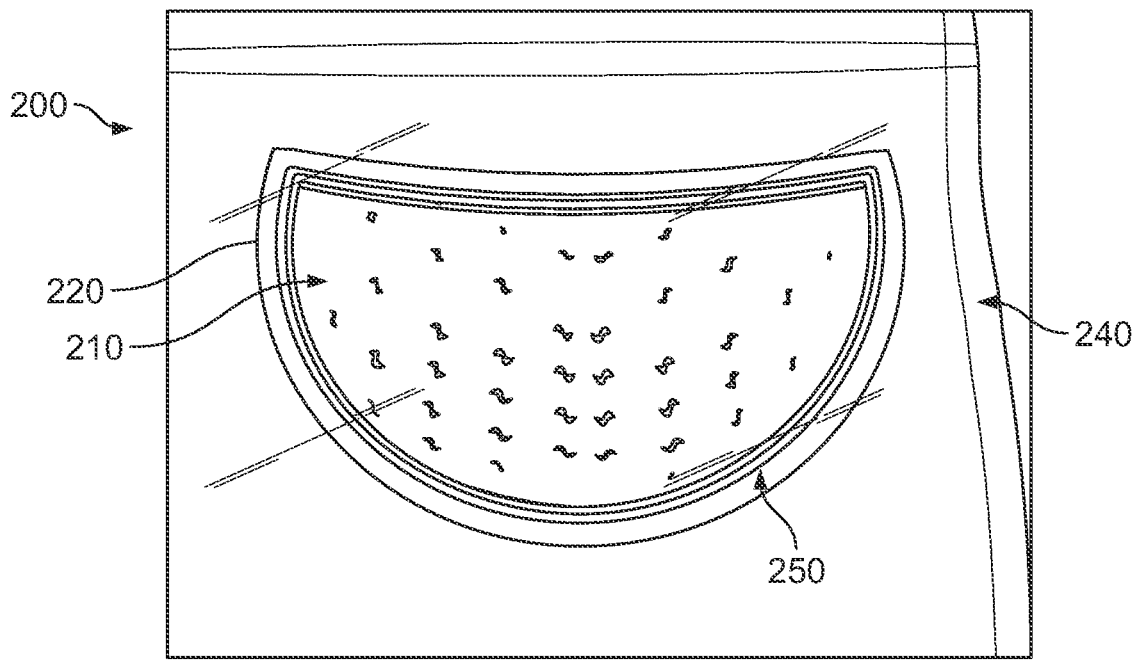

Processed tissue material 210 may include apertures 216 which extend through processed tissue material 210. As shown in FIGS. 5A and 5C, support 220 may be visible through apertures 216 in processed tissue material 210. In one example, processed tissue material 210 includes an internal matrix which is impregnated with one or more plasticizers, as set forth above. Plasticizing the tissue material may enable the tissue material to be manipulated, stretched, or bent during packaging, storage, or implantation.

In one example, a tension is applied to processed tissue material 210 prior to or during packaging. Processed tissue material 210 may be tensioned, for example, by being stretched overtop of the projection 228 of support 220. Processed tissue material 210 may also be held under tension by friction or holding force from support 220 and/or packaging material 240. In another example, packaging material 240 may be crimped or pressed against processed tissue material 210 in order to apply a tension to processed tissue material 210. The tension may be sufficient to stretch apertures 216 in processed tissue material 210 such that support 220 or packaging material 240 is visible through apertures 216, as shown in FIG. 5A.

An amount of tension suitable for processed tissue material 210 may be dependent on an intended implantation location or use of processed tissue material 210, and may be measured based on a change in any dimension (e.g. length, width) of processed tissue material 210. A suitable tension to be applied to processed tissue material 210 may be, for example, a tension that results in an elongation of a dimension of processed tissue material 210 by 0-75% or more, including 1%, 2%, 3%, 5%, 7%, 10%, 12%, 15%, 20%, 25%, 30%, 35%, 40%, 45%, 50%, 60%, or 70% or more. Providing the soft tissue material tensioned and packaged may assist in aligning the collagen fibrillar ultrastructure in preparation for the intended application and minimize time spent tensioning and processing the graft in the operating room. With the processed tissue material under tension in the packaging, the soft tissue graft may be delivered at its implant dimensions, removing guess work related to size changes.

Packaging material 240 encloses processed tissue material 210 and support 220. Packaging material 240 is formed from a flexible, strong material to facilitate easy handling and storage of the processed tissue material while maintaining a sterile environment therein. As shown in FIG. 5C, one or more portions of packaging material 240 may be transparent or translucent in order to enable viewing of processed tissue material 210 within packaging material 240. Packaging material 240 may further be formed from a biocompatible material, in order to prevent possible adverse reaction following implantation of processed tissue material 210. Suitable biocompatible materials for use as packaging material 240 include, for example, metals such as foil, plastic such as polyethylene, polyester, or acrylonitrile-butadiene-styrene (ABS), polytetrafluoroethylene (PTFE), ceramics such as aluminum oxide, or combinations of the foregoing materials, such as PET/AlO. Other suitable biocompatible materials will be apparent to those of skill in the art.

Figure 5D:
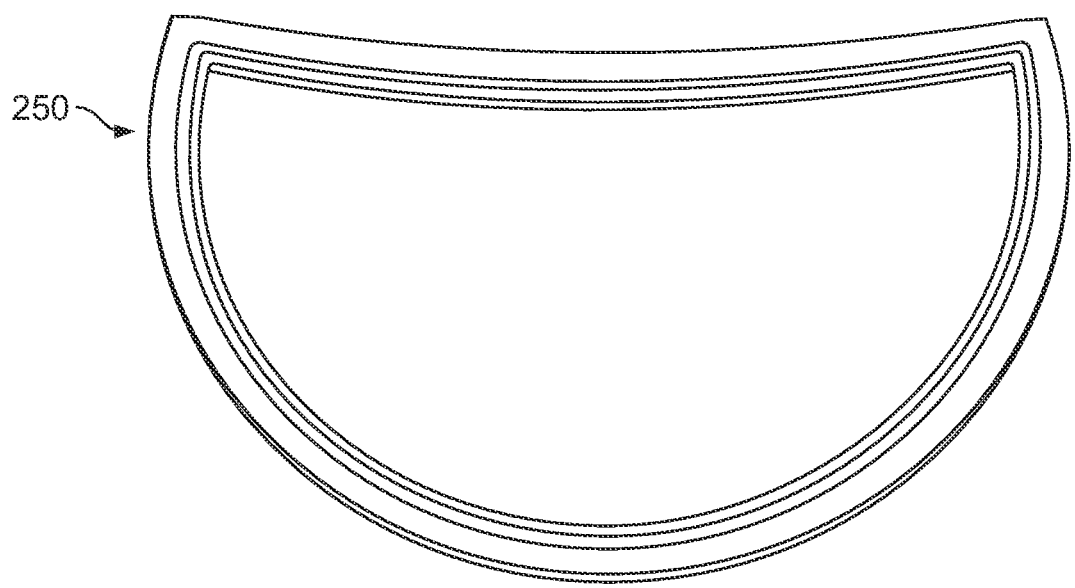

Processed tissue material 210 may include no apertures within a predetermined distance from edges of processed tissue material 210. As shown in FIGS. 5C and 5D, packaged soft tissue graft 200 may further include a frame 250 configured to surround processed tissue material 210. Frame 250 presses the edges of processed tissue material 210 (which may or may not include apertures 216) against support 220. Frame 250 may be configured to press processed tissue material 210 such that processed tissue material 210 is held under tension on support 220. Frame 250 may further be coupled to support 220 in order to secure processed tissue material 210 between support 220 and frame 250. Suitable structures for coupling frame 250 to support 220 include, for example, latches or other interlocking structures.

It will be understood that with hydrated and/or plasticized soft tissue grafts, post-packaging events such as shipping and storage can render the graft wrinkled, folded, slumped, etc. Providing frame 250 may provide a benefit of allowing the user to ascertain the true size and/or shape of the soft tissue graft before it is unpackaged, at which point it must be used or discarded.

Figure 6:
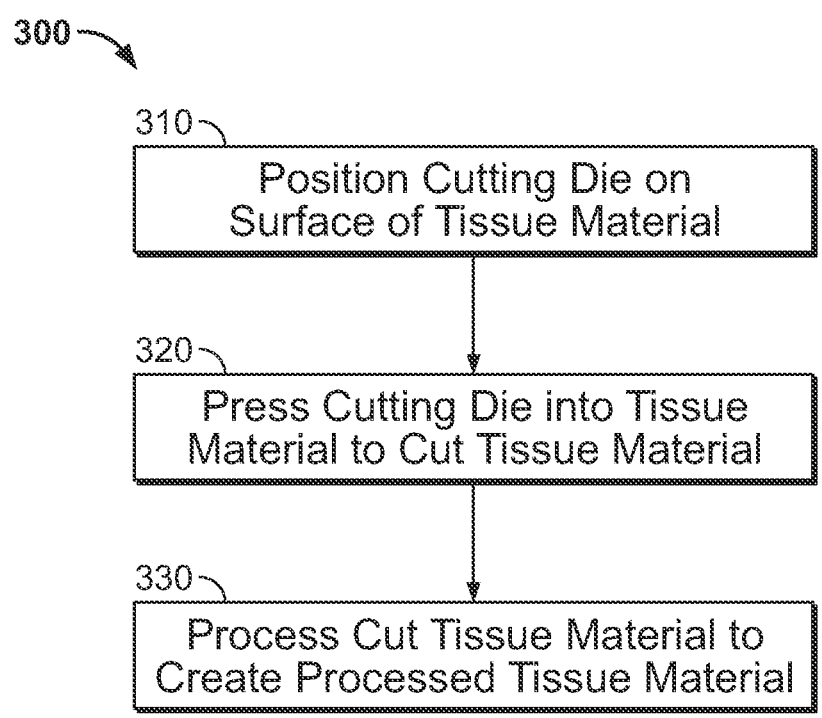
FIG. 6 shows a method of making a soft tissue graft.

FIG. 6 illustrates an example of a method 300 for making a soft tissue graft. The method includes positioning a cutting die, pressing the cutting die, and processing tissue material. Details regarding method 300 are set forth below.

In step 310, a cutting die is positioned on a surface of tissue material. The cutting die may define an outer edge of the resulting soft tissue graft, apertures to be cut into the soft tissue graft, or both. For cutting outer edges of the soft tissue graft, the blades of the cutting die may be sized to cut all of the way through the tissue material. For cutting apertures of the soft tissue graft, the blades of the cutting die may be sized to cut all of the way through the tissue material, or may be sized to cut only part of the way through the tissue material, depending on the desired depth of the apertures in the soft tissue graft.

Figure 7:
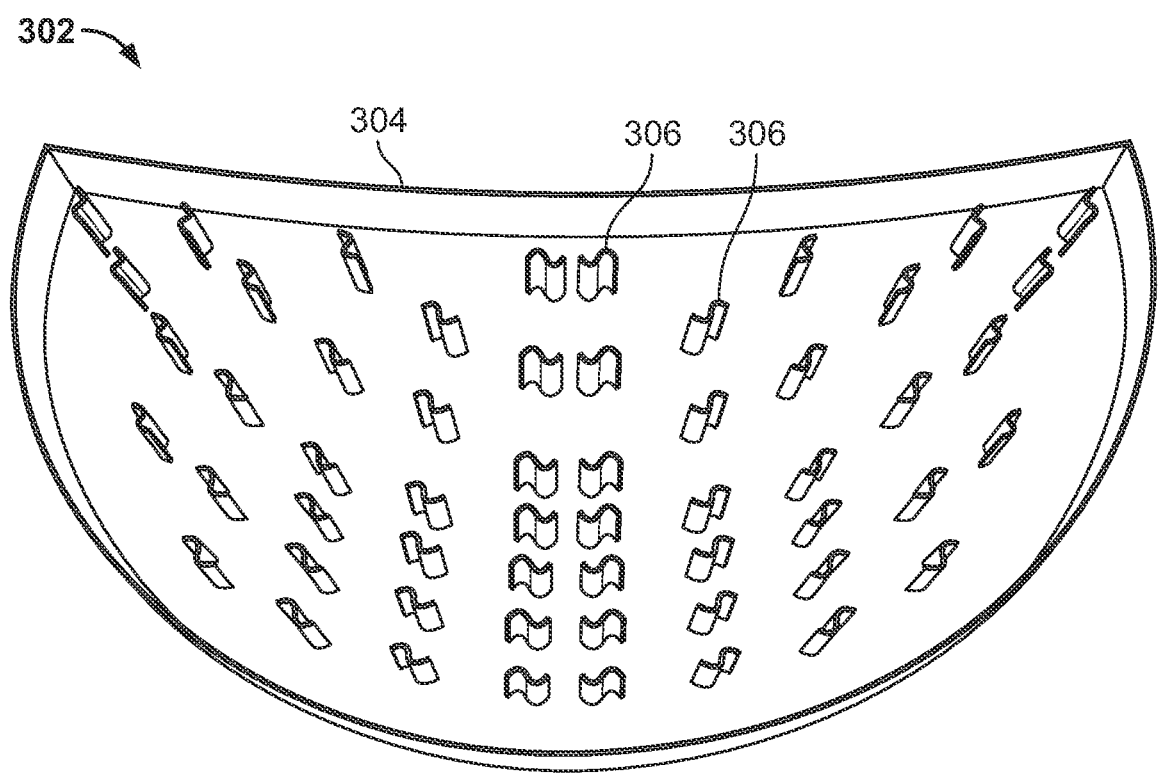
FIG. 7 shows an example of a cutting die for use in the method of FIG. 6.

An example cutting die 302 for use in method 300 is shown, for example, in FIG. 7. Cutting die 302 includes a first portion 304 for cutting outer edges of the soft tissue graft, and a plurality of second portions 306 for cutting apertures in the soft tissue graft. In the example of FIG. 7, first portion 304 and second portions 306 are not coupled to one another. However, it will be understood that first portion 304 and second portions 306 could be connected to one another or integrally formed with one another.

Prior to cutting, the tissue may be prepared to improve the ease or effectiveness of cutting. Such preparation may include cooling or freezing, freeze-drying, crosslinking, stretching, or being placed and held between two rigid or semi rigid surfaces. Tissue material may also be kept hydrated and/or wet prior to cutting in order to promote cutting of the tissue material.

Figure 8:
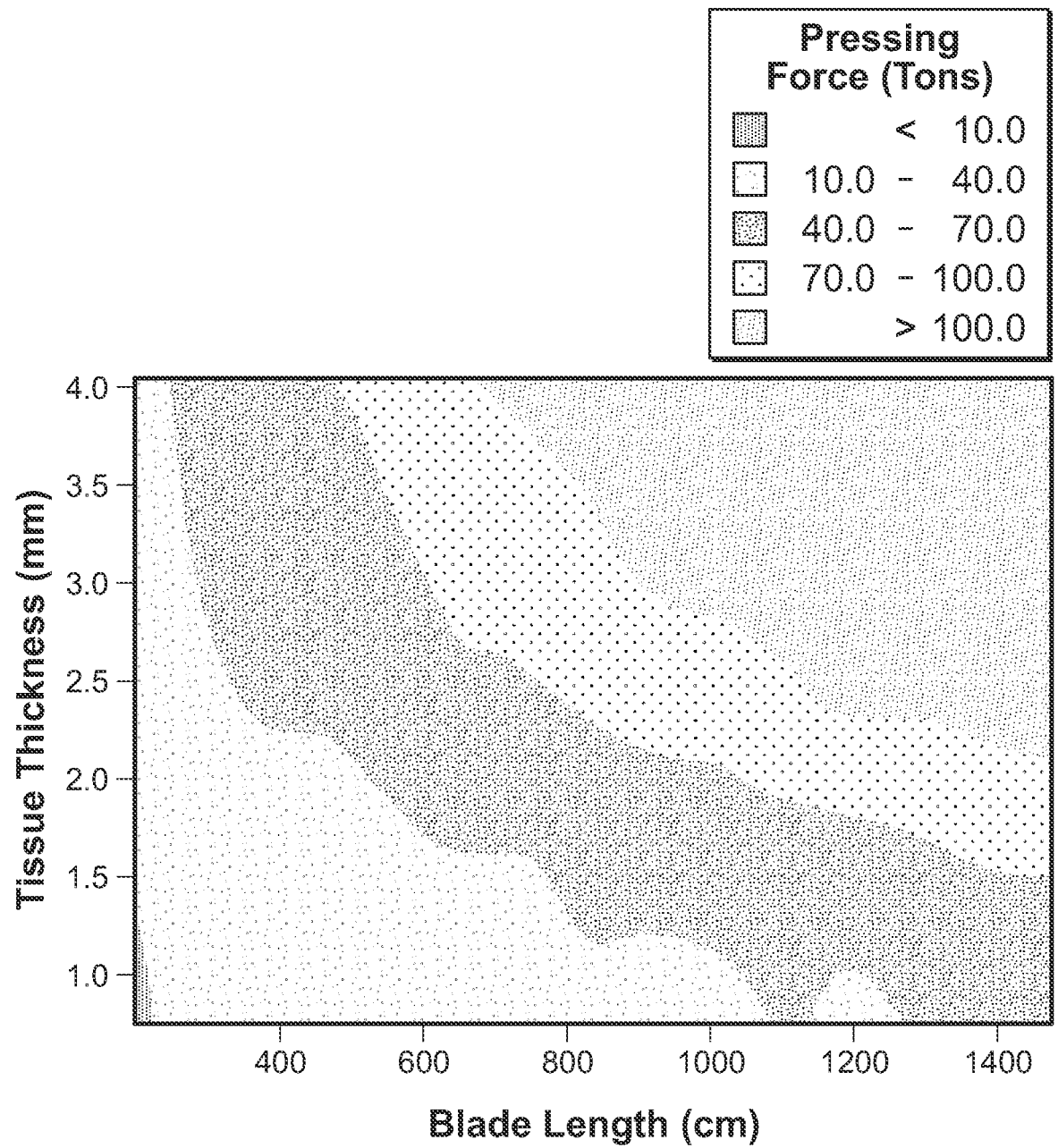
FIG. 8 shows a graph of guidelines for pressing force relative to tissue thickness and cutting die blade length for the method of FIG. 6.

In step 320, the cutting die is pressed into the tissue material to cut the tissue material. The cutting die must be pressed with sufficient force to cut through the tissue material. In one example, the cutting die is pressed by a hydraulic press. The hydraulic press may press the cutting die with a force of up to 10 tons, 20 tons, 30 tons, 40 tons, 50, tons 60 tons, 70 tons, 80 tons, 90 tons, 100 tons, or more, dependent on the thickness of the tissue material being cut and the length of the blades on the cutting die. An example graph of pressing force based on tissue thickness and blade length is shown in FIG. 8.

The cutting die may cut the outer edges of the soft tissue graft, apertures of the soft tissue graft, or both. If cutting is done in one stage, the cutting die may cut the outer edges and apertures simultaneously. If cutting is done in multiple stages, one cutting die may be used to cut outer edges of the soft tissue graft, and another cutting die may be used to cut the apertures of the soft tissue graft.

For cutting outer edges of the soft tissue graft, the blades of the cutting die may be sized to cut all of the way through the tissue material. For cutting apertures of the soft tissue graft, the blades of the cutting die may be sized to cut all of the way through the tissue material, or may be sized to cut only part of the way through the tissue material, depending on the desired depth of the apertures in the soft tissue graft.

The process of cutting the tissue material need not be limited to cutting tissue material for a single soft tissue graft, but may encompass cutting a plurality of separate portions from a tissue material. In additional examples, the tissue material not used to make the processed tissue material can be cut into reinforcement pieces to be stitched to the processed tissue material. Thus, the method may further comprise cutting reinforcement pieces from the tissue material after the cutting the plurality of cut tissue materials. The utilization of the tissue material may be characterized by the percentage of the tissue material used in making the processed tissue materials and/or reinforcement pieces. Such tissue material utilization may be at least 60, 65, 70, 75, 80, 85, 90, 95, 98 or 99%.

In step 330, the cut tissue material is processed to create processed tissue material. Suitable processes for step 330 are set forth above, and may include cleaning the cut tissue material, disinfecting the cut tissue material, removing cellular elements and small molecular weight solutes from the cut tissue material (i.e. "decellularizing" the cut tissue material), plasticizing the cut tissue material, packaging the cut tissue material, and/or sterilizing the cut tissue material.

Examples of a number of processes for step 330 are set forth below. It will be understood that these processing steps may occur at any point during making of the processed tissue material, including before or after cutting of the tissue material.

Processing the tissue material may include cleaning and disinfecting the tissue material with antibiotic and/or antimicrobial agents, and/or removing extraneous tissues associated with the tissue material, for example, including adipose, epithelial or epidermal tissues, prior to cutting the tissue material. The thickness of the tissue may be reduced prior to the cutting step by cutting or skiving the tissue material, for example, to create multiple thinner processed tissue materials for easier press cutting. The skived tissue material may optionally include the basement membrane and may also have a reticular side. Skiving may create a piece with a uniform thickness or allow for different thicknesses within a processed tissue material, such as thicker boarders. Skiving may be achieved with a rotating circular blade or an oscillating or band saw like straight blade or other cutting blade as described above. The tissue material may be held or fastened to a surface to aid in skiving by use of a vacuum table, clamp table, pin board, or any combination. Additionally, the skin may be prepared to improve cutting by cooling or freezing, free drying, or crosslinking, stretching, or being placed and held between two rigid or semi rigid surfaces.

Tissue materials may be washed with distilled/deionized endotoxin-free water and/or an aqueous solution, such as isotonic saline, among others. Multiple "washes" or "cleaning" may be affected using volumes of aqueous solution that are 2, 5, 10, 20 or 30 times the approximated volume of the tissue being processed, in some examples. The use of three such washing or cleaning steps may affect an approximate 1:100, 1:500 or 1:1000 dilution of associated solubilizable elements rendering the tissue essentially free from such solubilizable elements. In another aspect, the processing step described herein may also comprise devitalizing or decellularizing the tissue material to remove cellular components in accordance with the methods described in U.S. Pat. Nos. 6,734,018, 7,338,757, 8,574,826, 6,743,574, and 8,563,232, and U.S. Patent Application Publication No. 2014/0065238 and 2014/0154663, each of which is incorporated by reference herein in its entirety.

A devitalization process may be performed after cutting of the processed tissue material without damage to matrix and/or tissue structure of the tissue material and may employ detergents, sarcosinates, endonuclease, and decontaminating agents. The matrix structure may include collagens, hyaluronins, elastins, mucopolysaccharides and proteoglycans, among other components. In another aspect, the processing described herein may also comprise sterilizing the tissue material. Sterilization may involve the use of ionizing radiation, in some examples. In other examples, the absorbed dose of ionizing radiation may be between 8.0 KGy and 50 KGy, between 8.0 KGy and 25 KGy, or between 8.0 KGy and 18 KGy. In some examples, the sterilizing step may include placing a packaged graft on dry ice and irradiating the packaged product. In certain examples, sterilization may be performed at a temperature of between −20° C. and −50° C. The processed tissue material described herein may be sterilized using gamma irradiation, supercritical carbon dioxide, ethylene oxide, or electronic-beam.

The processing described herein may further comprise treating the tissue material with a water replacing agent. The water replacing agent may comprise one or more selected from the group consisting of glycerol (glycerin USP), adonitol, sorbitol, ribitol, galactitol, D-galactose, 1,3-dihydroxypropanol, ethylene glycol, triethylene glycol, propylene glycol, glucose, sucrose, mannitol, xylitol, meso-erythritol, adipic acid, proline, hydroxyproline, polyethylene glycol, alcohol, and lipids. The processing described herein may further comprise plasticizing the tissue material according to the teachings of one or more of U.S. Pat. Nos. 6,293,970, 6,569,200, 6,544,289, 7,063,726, or U.S. Patent Application Publication Nos. 2010/0030340, 2014/0180437, 2011/0015757, and 2013/0218294, each of which is incorporated herein by reference by its entirety.

The processing described herein may also comprise treating the tissue material with one or more treatment solutions before or after freezing and/or freeze drying. The processing described herein may also comprise treating the tissue material with one or more treatment solutions after freezing and/or freeze drying before implantation. The treatment solution may comprise an ionic, enzymatic, chemical crosslinking agent, a photoactive agent, or a polymer. The ionic crosslinking agent may comprise one or more selected from the group consisting of calcium, barium, aluminum, strontium, copper, zinc, magnesium, manganese, cobalt, and iron. The enzymatic crosslinking agent may comprise one or more selected from the group consisting of transglutaminase, ethylenediamine, lysyl oxidase family, hexamethylene diisocyanate (HMDIC), dimethyl (DMS), suberimidate and dimethyl-3-3'-dithiobispropionimidate (DTBP). The chemical crosslinking agent may comprise one or more selected from the group consisting of glutaraldehyde, glyceraldehyde, genipin, glucose or ribose, poly(ethylene glycol) diepoxide crosslinker, poly(ethylene glycol) diglycidyl ether, EDC and NHS, and acryl azide. The polymer may comprise one or more selected from the group consisting of native or modified collagen, gelatin, agarose, modified hyaluronic acid, fibrin, chitin, biotin, avidin, demineralized bone matrix, MATRIGEL®, HUMAN EXTRACELLULAR MATRIX™, proteoglycans, laminin, fibronectin, elastin, heparin, glycerol, sucrose octasulfate, polyethylene glycol, polymethylmethacrylate, polyurethane, acryloilmorpholine, N,N-dimethyl acrylamide, N-vinyl pyrrolidone and tetrahydrofurfuryl methacrylate, hydroxyapatite, polyurethane, and polylactic acid.

The processing described herein may also comprise adding one or more bioactive supplement(s) to the tissue material. In some examples, the one or more bioactive supplement(s) is selected from a group consisting of a growth or differentiation factor of the FGF family, TGF-family, IGF-1, PDGF, EGF, VEGF, HGF, PTHrP, Ihh, dexamethasone, insulin, transferrin, selenium, ITS, or ascorbate. The bioactive supplements may be growth factors, differentiation factors, cytokines, anti-microbial agents, or anti-inflammatory agents. The growth or differentiation factors may be for example, a growth factor of the FGF-family or TGF-family, IGF-1, PDGF, EGF, VEGF, HGF, PTHrP, Ihh (Indian Hedgehog Homolog), dexamethasone, insulin, transferrin, selenium, ITS supplement, ascorbate, or a combination thereof. The cytokines may include GM-CSF, G-CSF, TNF-α, IL-1β, IL-4, IL-6, IL-8, IL-10, SLP1, MCP1, MIP-1α, MIP-2, IL-18, angiopoietin, KGF, endothelin, IFN-α, or IFN-β. Examples of anti-inflammatory agents may include an IL-1βR antibody, TNF-α receptor antagonist, cyclooxygenase-2 specific inhibitors, MAP kinase inhibitors, NO synthase inhibitors, NF-κB inhibitors, or inhibitors of MMP. There are various fibroblast growth factors. As an example, the human FGF-family includes 22 members, FGF-1 through FGF-23. Examples of members of the TGF-family may include TGF-α and TGF-β superfamily. The TGF-β superfamily includes TGF-βs (such as TGF-β1, TGF-β2, TGF-β3), activins, inhibins, bone morphogenic factors (BMPs), modified BMPs, anti-mullerian hormone (AMH), myostatins, and others. There are 20 isotypes of BMPs. They may be separated into four subfamilies, for example, (1) BMP2 and BMP4; (2) BMP3 and BMP3B (also known as growth/differentiation factor 10 (GDF10)); (3) BMPs 5, 6, 7 and 8; and (4) GDFs 5, 6, and 7.

The processing described herein may also comprise adding one or more bioactive supplement(s) extracted from tissue comprising demineralized bone matrix, basement membrane, or submucosa matrix. In further examples, the method described herein may also comprise adding one or more antioxidants including, for instance, sodium nitroprusside, cartilage matrix glycoprotein (CMGP), vitamins C, vitamin E, selenium, N-Acetylcysteine (NAC) estradiol, glutathione, melatonin, resveratrol, flavonoid, carotene, aminoguanidine, or lycopene to protect bioactive components from oxygen-radical-induced damage antioxidants.

The processing described herein may also comprise adding one or more agent(s) that have bioactive supplement binding site(s) to the tissue material. In some examples, the agents having bioactive supplement binding site(s) may comprise hyaluronan, heparin, heparin sulfate, keratin sulfate, dermatan sulfate, chondroitin sulfate, betaglycan, heparan sulfate proteoglycan, syndecan, biglycan, or decorin. In additional examples, the agent(s) that have bioactive supplement binding site(s) increases the affinity of growth factors, differentiation factors, cytokines, anti-microbial agents, or anti-inflammatory agents to the tissue material.

Method 300 is not limited to the above steps, but may include alternative or additional steps, as would be understood from the description herein.

In order to facilitate processing of the tissue material, method 300 may further include positioning the tissue material in a bag. In one example, the tissue material is positioned in a bag which may later be used for packaging the tissue material. The tissue material may be placed on a cutting pad within the bag to avoid cutting of the bag underneath the tissue material. Positioning tissue material in a bag allows the tissue material to be kept hydrated during the cutting process, which may promote cutting of the tissue material. The cutting die may be positioned in the bag on the surface of the tissue material. In this example, the pressing may comprise pressing the outer surface of the bag to press the cutting die into the tissue material. The press may directly contact the outer surface of the bag, or may press a plate positioned against the outer surface of the bag, in order to avoid direct contact between the press and the bag. Additionally, a plate may be placed inside the bag on top of the cutting die to avoid accidental cutting of the top of the bag by the top of the cutting die. Following pressing, the cutting die and cutting pad are removed from the bag. The cut tissue material may then be processed in the bag, and the bag may then be sealed with the processed tissue material inside. Method 300 may further comprise storing the tissue material prior to implanting. In some examples, the processed tissue material is stored in a dry state, in cryopreservation, or in a wet state within the bag. The processed tissue material may be stored at room temperature prior to and up until implantation.

FIGS. 9 and 10 illustrate another example of a soft tissue graft 400. Soft tissue graft 400 may be suitable for use in mastopexy or breast reconstruction surgery. Soft tissue graft 400 is formed from processed tissue material 410. Details regarding soft tissue graft 400 are set forth below.

As shown in FIG. 9, processed tissue material 410 comprises a meshed tissue material. The meshed tissue material has a plurality of apertures 450. Apertures 450 may have any of the shapes or sizes set forth above with respect to apertures 150. In one example, apertures 450 are all of substantially the same size, e.g., within a size variation from an average aperture size of 10% or less. The density of apertures 450 in the meshed tissue material is 100, 80, 60, 40, 20, 10, 5 or 2 apertures/cm² of the tissue material or more, and 200, 150, 90, 70, 50, 30, 10 or 5 apertures/cm² of the tissue material or less. The density of apertures 450 in the meshed tissue material may also be from 2 to 200, from 5 to 10, from 10 to 100, from 1 to 300, from 15 to 150, from 15 to 40, or from 20 to 70 apertures/cm² of the tissue material. In some examples, when the processed tissue material 410 comprises the meshed tissue material, graft 400 has a plurality of apertures that form from 1, 5, 10, 15, 20, 25, 30, 35, 40, 45, 50, 55, 60, 65 or 70% to 35, 40, 45, 50, 55, 60, 65, 70, 75, 80, 85, 90 or 95% opening area based on the total area of processed tissue material 410. Apertures 450 may form from 4% to 98%, 10% to 80%, 30% to 70%, 40% to 60%, or 48% to 54% opening area based on the total area of the processed tissue material 410.

Figure 9A:
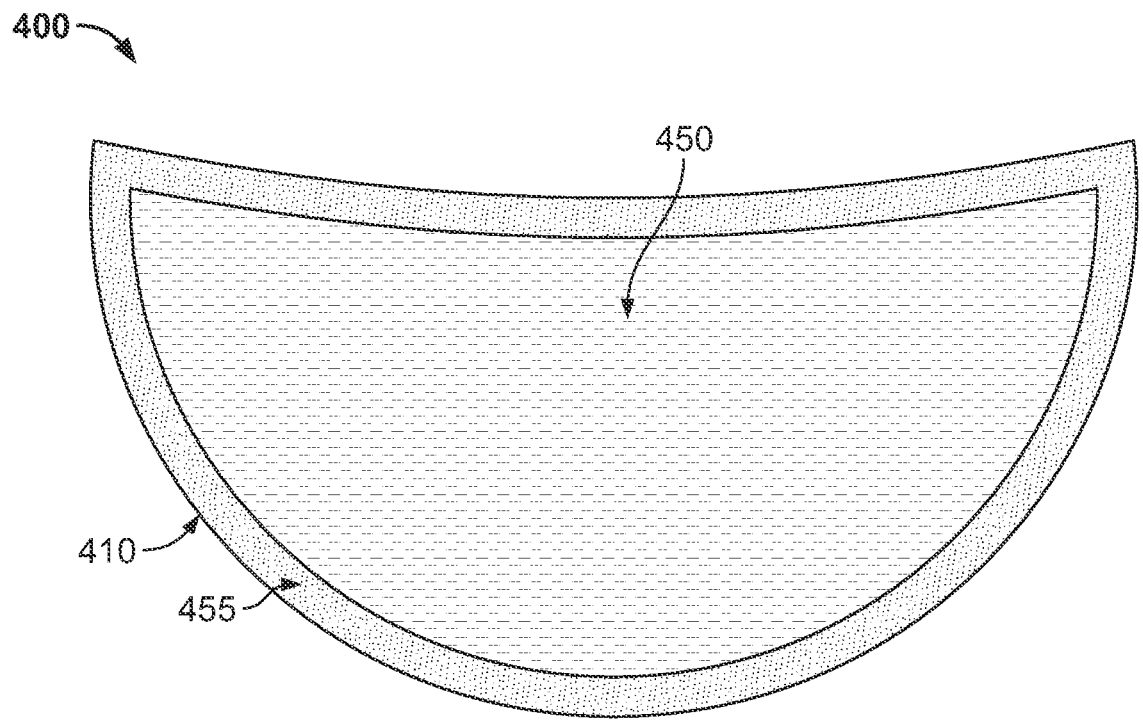
FIGS. 9A and 9B show examples of another soft tissue graft.
Figure 9B:
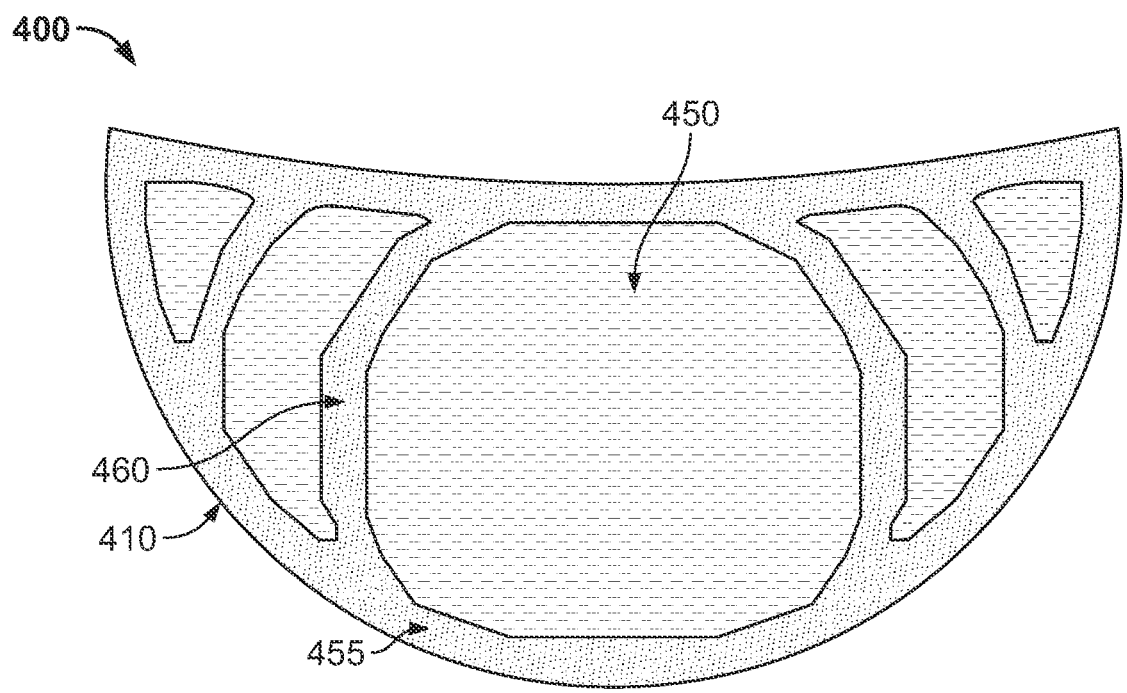

The meshed tissue material includes a plurality of linear apertures arranged in closely spaced rows and/or columns. In the example of FIGS. 9A and 9B, the linear apertures in the meshed tissue material are arranged extending in a length (or horizontal) direction of processed tissue material 410. This arrangement may promote elongation of processed tissue material 410 in a width (or vertical) direction of processed tissue material 410, while limiting elongation of processed tissue material in a length (or horizontal) direction, when compared to non-meshed tissue material.

Figure 10A:
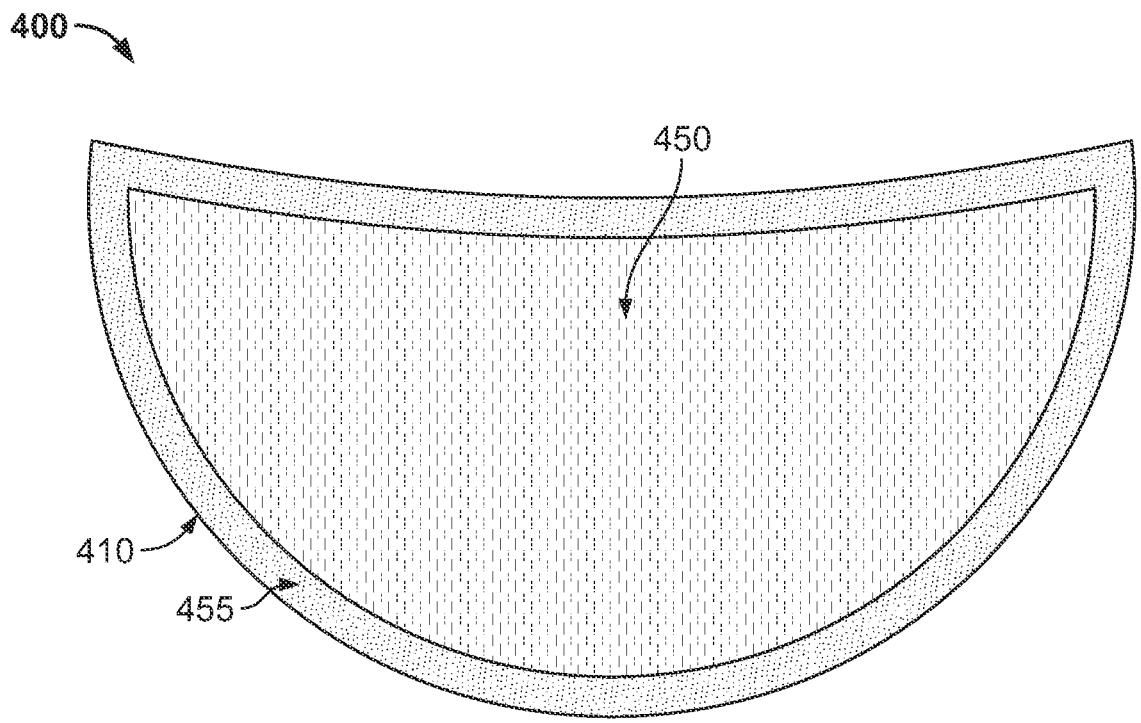
FIGS. 10A, 10B, and 10C show examples of yet another soft tissue graft.
Figure 10B:
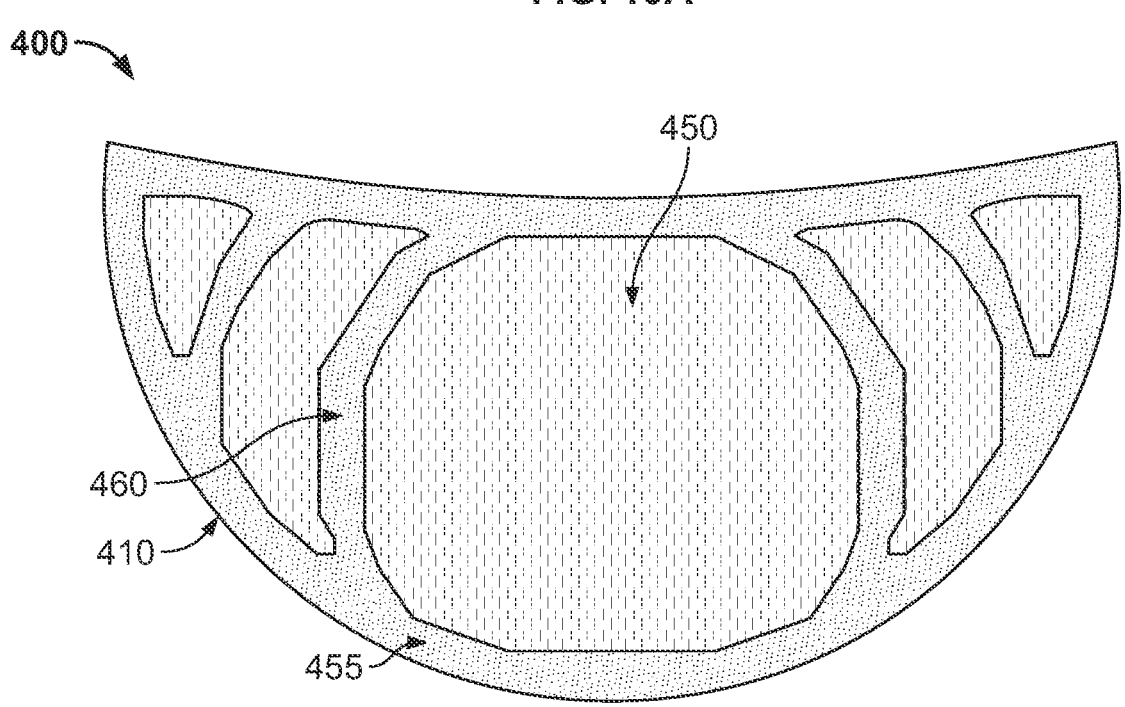
Figure 10C:
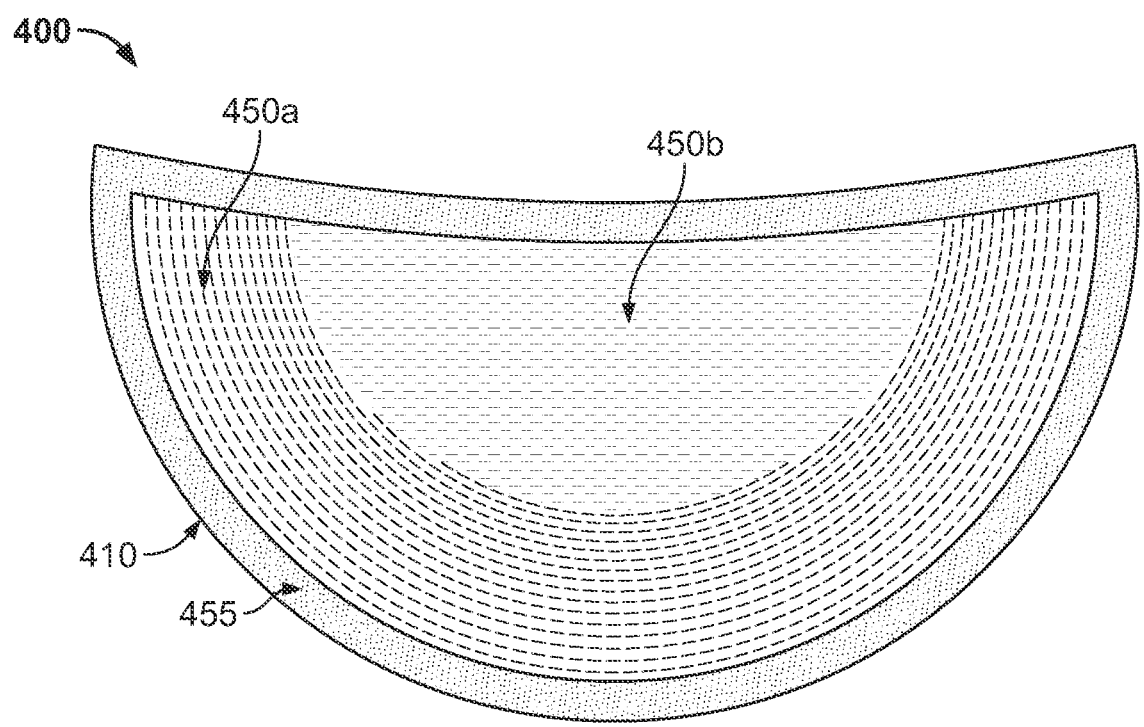

The orientation of apertures 450 is not intended to be limiting. In the example of FIGS. 10A and 10B, the linear apertures in the meshed tissue material are arranged extending in a width (or vertical) direction of processed tissue material 410. This arrangement may promote elongation of processed tissue material in a length (or horizontal) direction of processed tissue material, while limiting elongation of processed tissue material in a width (or vertical) direction, when compared to non-meshed tissue material. In the example of FIG. 10C, the linear apertures in the meshed tissue material are arranged different depending on their position in processed tissue material 410. As shown in FIG. 10C, a first group of apertures 450a adjacent the lower edge of processed tissue material 410 may be oriented to be parallel to the lower edge of processed tissue material 410, and a second group of apertures 450b spaced from the lower edge of processed tissue material 410 may be oriented to be parallel to the upper edge of processed tissue material 410. Other arrangements and orientations of apertures 450 will be apparent from the description herein.

As shown in FIGS. 9A-10C, processed issue material 410 may further comprise a tissue frame 455 attached to the meshed tissue material to prevent or decrease stretching of the meshed tissue material in at least one direction. In one example, tissue frame 455 is formed by not meshing or reducing the number of apertures during meshing in a frame area of a tissue material. In this example, tissue frame 455 may correspond in structure to the suture zone of processed tissue material 100. Processed tissue material 410 may further include one or more bands 460 corresponding in structure to the reinforcement bands 160 of processed tissue material 100.

In another example, tissue frame 455 may be formed separately with the processed tissue material described herein or with synthetic material, for example, including polyglycol, PTFE, polypropylene, and polyethylene, and sutured, sewed, or adhered to a meshed tissue material. In further examples, the frame may have a different number and/or area of apertures as the meshed tissue material described herein. For example, the frame may have from 0 to 2, from 1 to 2, from 1 to 10, from 1 to 20 apertures, and/or the apertures may form from 0 to 30%, from 0 to 5%, 1 to 20%, from 3 to 10% opening area based on the total area of the frame. Processed tissue material 410 may comprise 0, 1, 2, 3, 4, 5, 6, 7, 8, 9, 10, 20, 30, or 40 frames, and the total area of frames per graft may be from 1, 3, 5, 8, 10, 13, 15, 18, 20, 25, 30, 35, 40, 45 or 50% to 3, 5, 7, 10, 16, 19, 21, 24, 27, 30, 33, 36, 39, 42, 45, 48, 51, 55 or 60% based on the total area of the graft. In some examples, one or more frames may be located or cover at least a part of one or more suture zones, as described above with respect to graft 10.

Processed tissue material 410 may be prepared by cutting through the tissue material, for example, with a mesher. For another example, a meshed tissue material with a frame forming a suture zone may be prepared by using a cutting die that has border blades to cut the outside border rim matching the shape of the blades, a blade-free area that render the suture zone, and blades in the center area to cut through and mesh the tissue material. A meshed tissue material with a frame forming a suture zone and a center connecting bands may be prepared by using a cutting die that has border blades to cut the outside border rim matching the shape of the blades, a blade-free area around the border rim that render the suture zone, blade-free areas in the center that render the bands, and blades in the center area to cut through and mesh the tissue material.

Figure 11A:
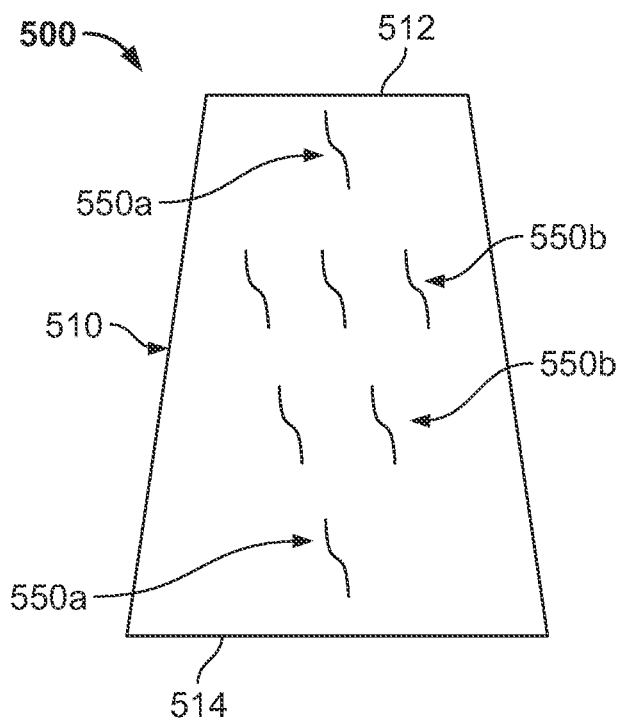
FIGS. 11A and 11B show examples of another soft tissue graft.
Figure 11B:
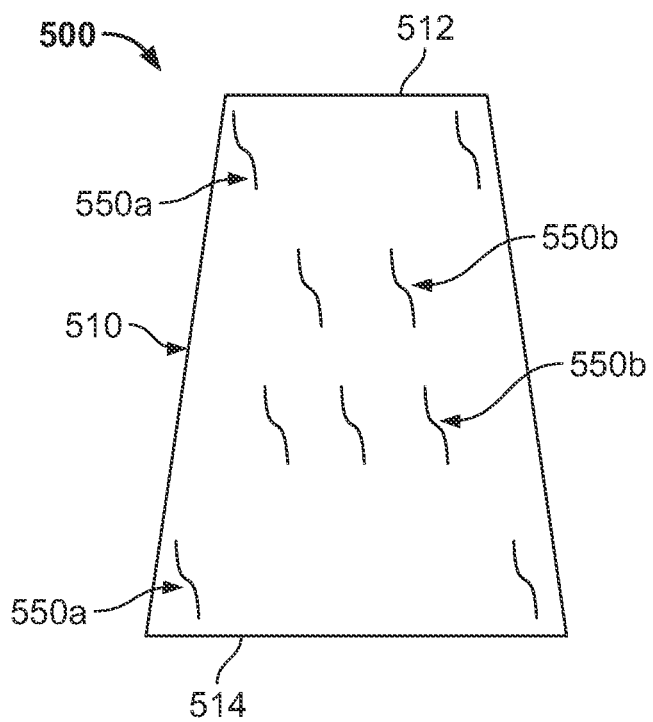

FIGS. 11A and 11B illustrate another example of a soft tissue graft 500. Soft tissue graft 500 may be suitable for use in rotator cuff repair, remodeling, augmentation, or enforcement, tendon and/or ligament repair or enforcement procedures, or capsular reconstruction. Soft tissue graft 500 is formed from processed tissue material 510. Details regarding soft tissue graft 500 are set forth below.

As shown in FIGS. 11A and 11B, processed tissue material 510 has a trapezoidal shape with parallel edges 512 and 514. However, processed tissue material 510 is not limited to having the shape shown in FIGS. 11A and 11B. Processed tissue material 510 may have any alternate shape suitable for the intended implantation procedure, including a quadrilateral or parallelogram shape.

Processed tissue material 510 further includes a plurality of apertures 550. Apertures 550 may have any of the shape, sizes, or layouts set forth above with respect to apertures 150.

In one example, processed tissue material 510 has a set of apertures 550a adjacent parallel edges 512 and 514, and a set of apertures 550b in a central region of processed tissue material 510. Apertures 550a may be the same or different from apertures 550b. In a further example, apertures 550a and 550b may extend only part of the way through processed tissue material 510, in order to preserve the biomechanical strength of graft 500. Apertures 550a may extend from an inferior or bottom surface of processed tissue material 510, to improve cellular infiltration and ingrowth at bony attachment points. Apertures 550b may extend from a superior or top surface of processed tissue material 510, in order to enhance cellular infiltration and neovascularization.

It will be understood that the location of apertures 550 shown in FIGS. 11A and 10B is provided for the purposes of illustration. Apertures 550 shown in FIGS. 11A and 10B may be repositioned, removed, duplicated. In one example, the positioning of one or more apertures 550 in FIG. 11A may be combined with the positioning of one or more apertures 550 in FIG. 11B in a single graft 500.

Figure 12A:
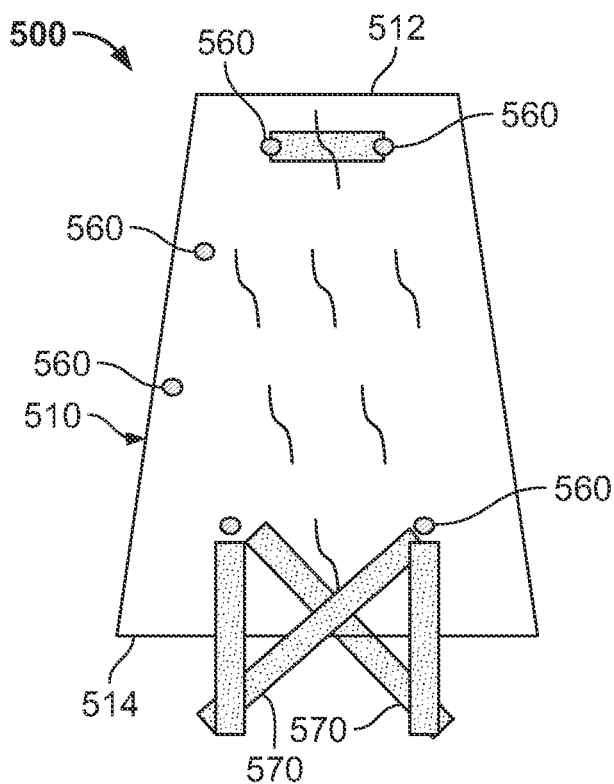
FIGS. 12A and 12B show examples of the soft tissue grafts of FIGS. 11A and 11B including operative modifications.
Figure 12B:
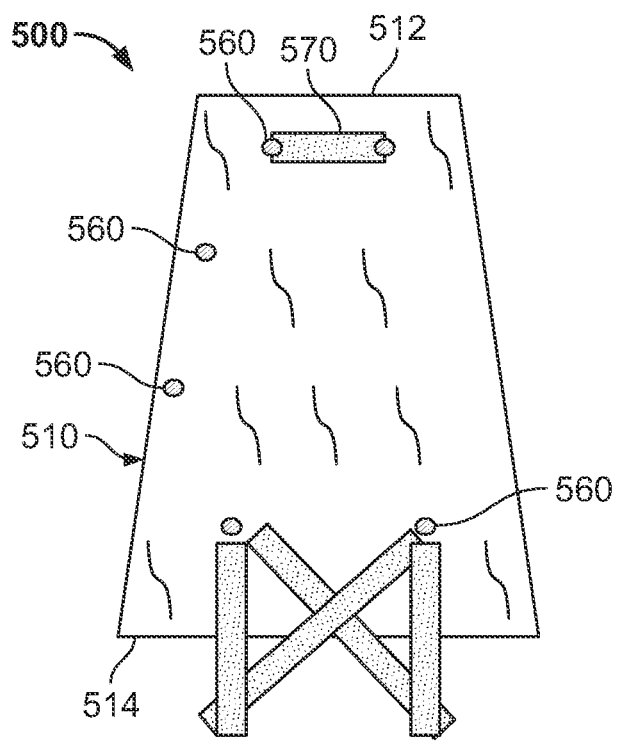

Soft tissue graft 500 may require one or more operative modifications during surgical implantation. FIGS. 12A and 12B show examples of operative modifications of soft tissue graft 500 during an example superior capsular reconstruction procedure. As shown in FIGS. 12A and 12B, it may be necessary to form one or more suture holes 560 in graft 500 for suturing graft 500 to the patient. It may further be necessary to thread sutures 570 through suture holes 560 to anchor graft 500 in the correct position during implantation. Suture holes 560 may be provided on graft 500 in advance of surgery, or may be created intra-operatively during implantation of graft 500.

A method of implanting a soft tissue graft in a patient is disclosed. The method comprises optionally stretching a soft tissue graft, and stitching the soft tissue graft on a predetermined location of the patient. The soft tissue graft may be any of the soft tissue grafts described herein. In a mastopexy or breast reconstruction procedure, the soft tissue graft may be stitched onto the chest wall of the patient. Where the graft includes a suturing zone and or reinforcement bands, the stitching may be performed within the suturing zone(s) and/or reinforcement band(s) of the graft.

In one example, the soft tissue graft may be three dimensionally stretched on the surface, for example, of a breast implant to form a stretched graft. Upon stretching, the graft would no longer be in a two dimensional plane, but would be in a three dimensional form having a contour of the site of implantation (e.g. contour of a synthetic breast implant at the site of the implantation). Also upon stretching, apertures in the graft may be stretched to form openings in the graft. An average size of the opening area formed by the apertures may increase upon stretching by 0, 0.1, 0.4, 0.5, 1, 5, 8, 10, or 15 mm$^2$ to 50, 100, 150, 180, 200, 300 or 400 mm$^2$.

In some examples, the method of implanting may further comprise stitching one, two, three, four or more reinforcement pieces onto the processed tissue material of the graft. The reinforcement pieces may be stitched to any corner and/or borders of the processed tissue material to increase their length or width. In other examples, the method may further comprise stitching at least two reinforcement pieces to two corners of the processed tissue material to form a reinforced graft having an increased length compared to the graft prior to the stitching.

The method of implanting may incorporate any of multiple different reconstructive techniques. Such techniques which utilize the described soft tissue grafts may include: (i) one stage sub muscular, or direct to implant procedure, (ii) two stage sub muscular, or tissue expander to implant procedure, and/or (iii) immediate implant-based prepectoral breast reconstruction.

With respect to the one stage sub muscular, or direct to implant procedure, for example, post-mastectomy, the inferior border of the processed tissue material is used to recreate the inframammary fold. The superior border is attached to the disinserted pectoralis major to create a complete sub pectoral, sub graft pocket for implant placement. The processed tissue material may provide numerous potential benefits. Complete implant coverage may reduce the risk of implant exposure, extrusion, visibility, and palpability. Tethering of the pectoralis major may prevent the implant from migrating and creating an unnatural breast step-off or fold effacement.

With respect to the two stage sub muscular, or tissue expander to implant procedure, for example, post-mastectomy, the inferior border of the processed tissue material is used to recreate the inframammary fold. The superior border may be attached to the disinserted pectoralis major to create a complete sub pectoral, sub graft pocket for the expander placement. The processed tissue material may provide numerous potential benefits. Complete expander coverage may allow for more intraoperative expansion volume as well as more rapid overall expansion. Additional benefits after the exchange from expander to implant may include reduce risk of implant exposure, extrusion, visibility, and palpability. Tethering of the pectoralis major prevents the implant from migrating and creating an unnatural breast step-off or fold effacement.

With respect to the immediate implant based prepectoral breast reconstruction, for example, post-mastectomy the lateral skin flap may be anchored to the serratus and pectoralis muscle by advancing the flap medially. Processed tissue material may be sutured to the superior medial and lateral edges of the pectoralis major muscle. The inferior edge may be sutured to the fascia at the level of the inframammary fold. The implant may be inserted in the newly created sub processed tissue material pocket. Post implant filling, the subcutaneous pocket may be dissected inferolaterally and the injection port secured. The lateral flap may be trimmed and advanced beneath the medial flap and sutured into position.

Another method of implanting a soft tissue graft in a patient is disclosed. The following method may be usable during a rotator cuff repair, remodeling, augmentation, or enforcement procedure, tendon and/or ligament repair or enforcement procedure, or capsular reconstruction. In particular, the method may utilize soft tissue grafts for repair, augmentation, reconstruction or enforcement of tendons and ligaments. Surgical procedures may include repair of rotator cuff, superior capsule reconstruction, repair of Achilles tendon rupture, repair of ruptured distal biceps (Bicep brachii), distal triceps tendon repair, reconstruction of Acromioclavicular joint or Coracoclavicular ligaments repair, and/or augmentation or repair of patellar and/or quadriceps tendon, latissimus dorsi tendon transfer, pectoralis major tendon.

Prior to surgery, the graft is provided preshaped to a suitable size, shape and thickness for the application and arthroscopic surgery to minimize time spent cutting and processing the graft in the operating room. For a rotator cuff repair and/or superior capsular reconstruction procedure, the graft may be provided with a trapezoidal shape having parallel edges. During the procedure, suture holes may be formed adjacent the parallel edges of the graft, and then the graft may be anchored to the underlying bone with sutures. Suitable suture hole locations as well as suturing procedures will be known to those skilled in the art.

For tendon and/or ligament repair procedures, the graft may be wrapped around the subject tendon or ligament to mechanically support the tendon or ligament. The graft may then be sutured in place wrapped around the tendon or ligament, to form a new outer surface for the tendon or ligament.

The graft is provided with apertures in order to provide increased locations for angiogenesis, enable ingrowth and remodeling without compromising biomechanical strength for the intended application. For rotator cuff repair and/or superior capsular reconstruction, apertures on the inferior surface enable ingrowth and remodeling at the bone tendon interface and apertures on the superior surface provide locations for ingrowth between soft tissues. For tendon repair, apertures wrapped against the tendon provide increased locations for ingrowth between the tendon and graft while the exterior of the graft remains smooth to maintain tendon glide and minimize adhesions.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," "includes," "including," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "a" or "an" does not, without further constraints, preclude the existence of additional identical elements in the process, method, article, or apparatus that comprises the element.

Unless otherwise stated, any and all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

While the foregoing has described what are considered to be the best mode and/or other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present concepts.

What is claimed is:

1. A soft tissue graft comprising:
processed tissue material having first and second opposed surfaces, the first and second opposed surfaces bounded by first and second edges, the first edge having a concave shape that curves toward the second edge, the second edge having a convex shape that curves away from the first edge, wherein the first surface is meshed to form a plurality of apertures with a predetermined density,
wherein the plurality of apertures are a plurality of linear apertures, and the plurality of linear apertures extend in a substantially vertical direction substantially parallel to a line bisecting each of the first edge and the second edge into two equal parts.

2. The graft of claim 1, wherein the first edge and the second edge share both ends.

3. The graft of claim 1, wherein the graft is symmetrical about the line bisecting the first and second edges.

4. The graft of claim 1, wherein the apertures extend all of the way from the first surface to the second surface.

5. The graft of claim 1, wherein the apertures are formed from a linear separation in the first surface.

6. The graft of claim 1, wherein the apertures are formed from a multi-directional separation in the first surface.

7. The graft of claim 1, wherein the apertures each have a same shape and size.

8. The graft of claim 1, wherein the apertures have a length of from 1 mm to 10 mm.

9. The graft of claim 1, wherein each of the apertures has an area of from 0.5 $mm^2$ to 200 $mm^2$.

10. The graft of claim 1, wherein a distance between adjacent apertures is from 0.5 mm to 30 mm.

11. The graft of claim 1, wherein a ratio of average distance between adjacent apertures to average length of the apertures is from 0.5 to 1.0.

12. The graft of claim 1, wherein an average thickness of the processed tissue material is from 0.1 mm to 10 mm.

13. The graft of claim 1, wherein the processed tissue material has a length of from 8 cm to 25 cm.

14. The graft of claim 1, wherein the processed tissue material has a width of from 2 cm to 22 cm.

15. The graft of claim 1, wherein no apertures are positioned within a predetermined distance from the first and second edges.

16. The graft of claim 1, wherein the processed tissue material is processed from human tissue.

17. The graft of claim 1, wherein the processed tissue material has an internal matrix, and one or more plasticizers are contained in the internal matrix.

* * * * *